(12) United States Patent
Kosai et al.

(10) Patent No.: US 8,034,589 B2
(45) Date of Patent: Oct. 11, 2011

(54) METHOD OF PREPARING A PROLIFERATION-REGULATED RECOMBINANT ADENOVIRAL VECTOR EFFICIENTLY AND KIT FOR PREPARING THE SAME

(75) Inventors: Kenichiro Kosai, Fukuoka (JP); Satoshi Nagano, Fukuoka (JP)

(73) Assignee: Nagoya Industrial Science Research Institute, Aichi (JP)

( * ) Notice: Subject to any disclaimer, the term of this patent is extended or adjusted under 35 U.S.C. 154(b) by 1294 days.

(21) Appl. No.: 10/567,010

(22) PCT Filed: Jul. 26, 2004

(86) PCT No.: PCT/JP2004/010998
§ 371 (c)(1),
(2), (4) Date: Aug. 9, 2006

(87) PCT Pub. No.: WO2005/012536
PCT Pub. Date: Feb. 10, 2005

(65) Prior Publication Data
US 2007/0036759 A1    Feb. 15, 2007

(30) Foreign Application Priority Data

Jul. 31, 2003 (JP) ................................. 2003-283427

(51) Int. Cl.
*C12N 15/64* (2006.01)
*C12N 15/861* (2006.01)

(52) U.S. Cl. .................................... 435/91.4; 435/320.1

(58) Field of Classification Search ........................ None
See application file for complete search history.

(56) References Cited

U.S. PATENT DOCUMENTS 6,692,736 B2 *   2/2004   Yu et al. ........................ 424/93.2
2003/0099616 A1   5/2003   Irving et al.

FOREIGN PATENT DOCUMENTS

JP    08-084589    4/1996
WO    WO 01/73093  10/2001

OTHER PUBLICATIONS

Mizuguchi, H. et al., "A Simple Method for Constructing E1- and E1/E4-Deleted Recombinant Adenoviral Vectors", 1999, H. Gene Ther., vol. 10: pp. 2013-2017.*
Hardy, S. et al., "Construction of Adenovirus Vectors through Cre-lox Recombination", 1997, J. Virol., vol. 71: pp. 1842-1849.*
Nagano, S. et al. "An efficient construction of conditionally replicating adenoviruses that target tumor cells with multiple factors", 2005, Gene Ther., vol. 12: pp. 1385-1393.*
Bischoff, Jr. et al., "An Adenovirus Mutant that Replicates Selectively in p53-Deficient Human Tumor Cells", *Science*, vol. 274, pp. 373-376, 1996.
Heise, c. et al., "An Adenovirus E1A Mutant that Demonstrates Potent and Selective Systemic Anti-Tumoral Efficacy", *Nature Medicine*, vol. 6, No. 10, pp. 1134-1139, 2000.
Kozai, K. et al., "Generation of Various Types of Tumor-Specifically Replicating Adenoviral Vector (rADV)", *Memorial Foundation Kenkyu Hokokushu*, vol. 16, pp. 465-466, 2002. (Partly translated).
Rodriguez, R. et al. "Prostate Attenuated Replication Competent Adenovirus (ARCA) CN706: A Selective Cytotoxic for Prostate-Specific Antigen-Positive Prostate Cancer Cells", *Cancer Research*, vol. 57, pp. 2559-2563, 1997.
Yu, DC. Et al., "Identification of the Transcriptional Regulatory Sequences of Human Kallikrein 2 and Their Use in the Construction of Calydon Virus 764, an Attenuated Replication Competent Adenovirus for Prostate Cancer Therapy", *Cancer Research*, vol. 59, pp. 1498-1504, 1999.

* cited by examiner

*Primary Examiner* — Michael Burkhart
(74) *Attorney, Agent, or Firm* — Occhiuti Rohlicek & Tsao LLP

(57) ABSTRACT

Provided is a method of preparing a proliferation-regulated recombinant adenoviral vector effectively, comprising preparing a proliferation-regulated vector plasmid by preparing a restriction enzyme-recognizing sequence in a vector plasmid having a proliferation-regulating unit and having an E1A region, a protein-coding region in a E1B region, a poly(A) signal sequence, and a recombinase-recognizing sequence in that order from upstream, by deleting an endogenous promoter in the E1A region or an endogenous promoter regulating expression of the protein-coding gene in one protein-coding region of the E1B region thereof and inserting the restriction enzyme-recognizing sequences in the deficient site, and introducing a promoter expressing specifically in a target organ in the restriction enzyme-recognizing sequence in the restriction enzyme-recognizing sequence; and additionally, integrating the proliferation-regulated vector plasmid into a vector plasmid having a adenoviral genome prepared by deleting the E1 region.

20 Claims, 9 Drawing Sheets

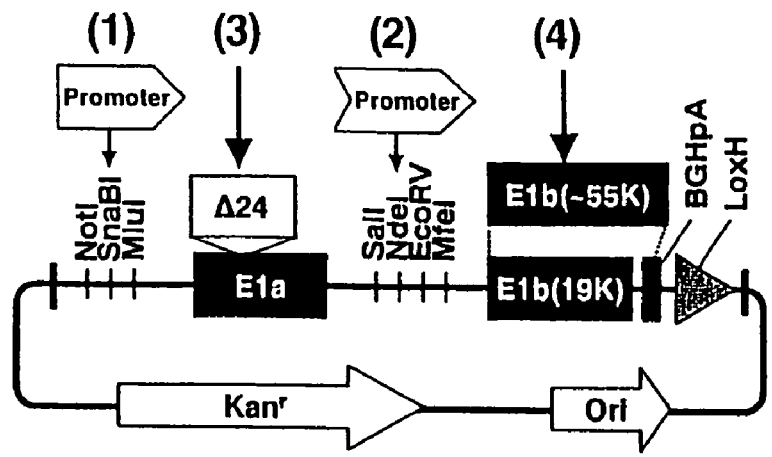
A. Vector plasmid having a proliferation-regulating unit
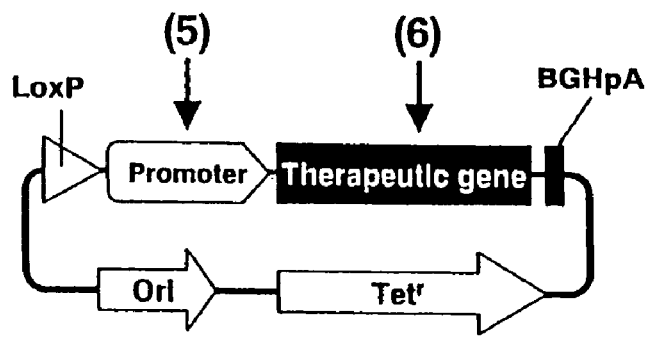
B. Vector plasmid having a therapeutic gene-expressing unit
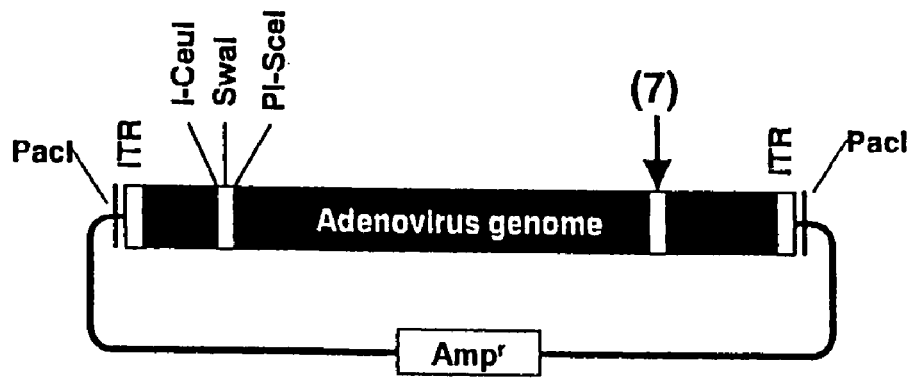
C. Adenoviral vector plasmid
Fig. 1

| Primer name | DNA sequence |
|---|---|
| S-E1A | 5'-TCAGTCGCATGCGCGGCCGCTACGTAACGCGTTACCCGGTGAGTTCCTCAAGAGGC-3'<br>Stuffer \| SphI \| NotI \| SnaBI \| MluI \| Ad5 474~497 |
| AS-E1A | 5'-GGACGTCCTAGGGTCGACGCCCCATTTAACACGCCATGCAAG-3'<br>Stuffer \| AvrII \| SalI \| Ad5 1635~1658 (AS) |
| S-E1B19K | 5'-TCAGTCCCTAGGGTCGACCATATGGATATCCAATTGCGTGGGCTAATCTTGGTTACATCT-3'<br>Stuffer \| AvrII \| SalI \| NdeI \| EcoRV \| MfeI \| Ad5 1684~1707 |
| AS-E1B19K | 5'-GGACGTGGATCCGCGTCTCAGTTCTGGATACAGTTC-3'<br>Stuffer \| BamHI \| Ad5 2262~2285 (AS) |
| S-BGHpA | 5'-TCAGTCGGATCCGCATGCATCTAGAGCTCGCTGATC-3'<br>Stuffer \| BamHI \| pRc/RSV 693~716 |
| AS-BGHpA | 5'-GGACGTGAATTCATAACTTCGTATAATGTATGCTATATGAGGTAATTCAGAAGCCCATAGAGCCCACCGCA-3'<br>Stuffer \| EcoRI \| LoxH (AS) \| pRc/RSV 933~956 (AS) |

<PCR condition>
Thermal denaturation 94°C, 30 seconds
Annealing 57°C, 30 seconds
Elongation reaction 74°C, 60 seconds
30 cycles

Fig. 2

| Primer name | DNA sequence |
|---|---|
| S-Δ24 | 5'-TTGTACCGGAGGTGATCGATCCACCCAGT-3'<br>　　　　　　　　｜　　　　｜<br>　　　Ad5 903~922　　Ad5 947~956 |
| AS-Δ24 | 5'-TCCTCGTCGTCACTGGGTGGATCGATCACC-3'　<PCR condition><br>　　　｜　　　　　｜　　　　　Thermal denaturation　94°C, 30 seconds<br>Ad5 966~947 (AS)　Ad5 922~913 (AS)　Annealing　　　　　　57°C, 30 seconds<br>　　　　　　　　　　　　　　　　　　Elongation reaction 74°C, 60 seconds<br>　　　　　　　　　　　　　　　　　　30 cycles |
| S-E1B-2015 | 5' ATAAATGGAGCGAAGAAACC 3'<br>　　　　｜<br>　　Ad5 2015~2034 |
| AS-E1B-4073 | 5' GGACGTGAATTCATAACTTCGTATAATGTATGCTATATGAGGTAATCTTGATCCAAATCCAAACAGAGTC 3'<br>　　｜Stuffer｜　EcoRI　｜　　　　　　LoxH (AS)　　　　　｜　　Ad5 4050~4073　(AS) |

Fig. 4

| Primer name | DNA sequence | |
|---|---|---|
| S-CMVp | 5'-TCAGTCGTCGACCGTTGACATTGATTATTGAC-3'<br>Stuffer \| SalI \| pRc/CMV 231~250 | |
| AS-CMVp | 5'-GGACGTCAATTGGCTTGGGTCTCCCTATAGTG-3'<br>Stuffer \| MfeI \| pRc/CMV 874~893 (AS) | |
| S-CEAp | 5'-TCAGTCGCGGCCGCATCATCCCACCTTCCCAGAG-3'<br>Stuffer \| NotI \| CEAp (−424~−405) | |
| AS-CEAp | 5'-GGACGTACGCGTCCAGGTCTCTGCTGTCTGC-3'<br>Stuffer \| MluI \| CEAp (AS, −19~+1) | |
| S-OCp | 5'-CTGCAGGGTCAGGAGGAGAA-3'<br>OCp (−834~−815) | |
| AS-OCp | 5'-GCGCTGGGCTGCTGCTCAGG-3'<br>OCp (+12~+31) | |

<PCR condition>

Thermal denaturation  94°C, 30 seconds

Annealing  57°C, 30 seconds

Elongation reaction 74°C, 60 seconds 30 cycles

Fig. 5

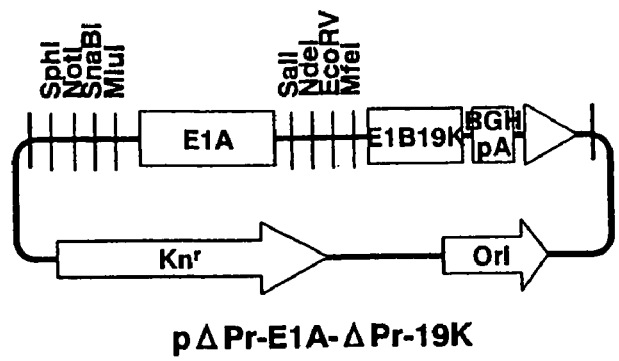
pΔPr-E1A-ΔPr-19K
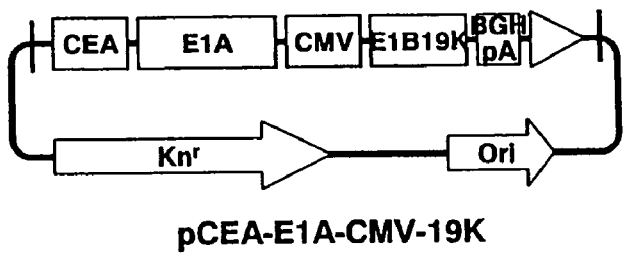
pCEA-E1A-CMV-19K
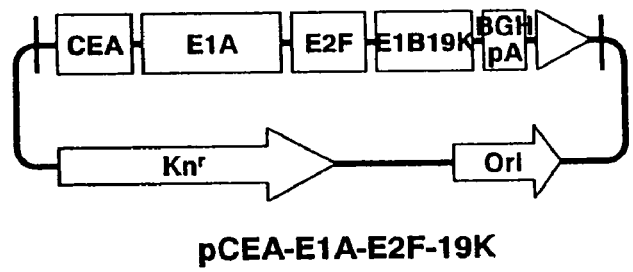
pCEA-E1A-E2F-19K
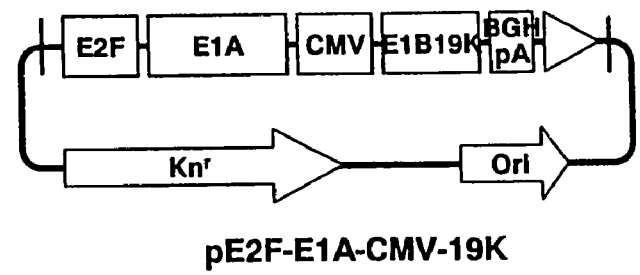
pE2F-E1A-CMV-19K
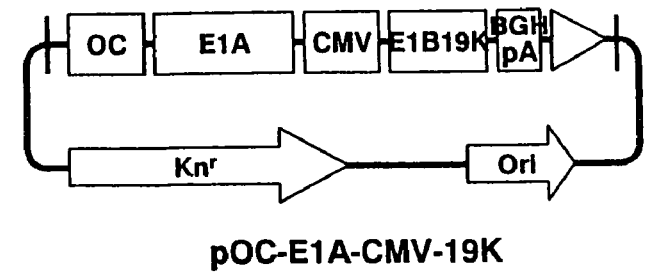
pOC-E1A-CMV-19K
Fig. 6

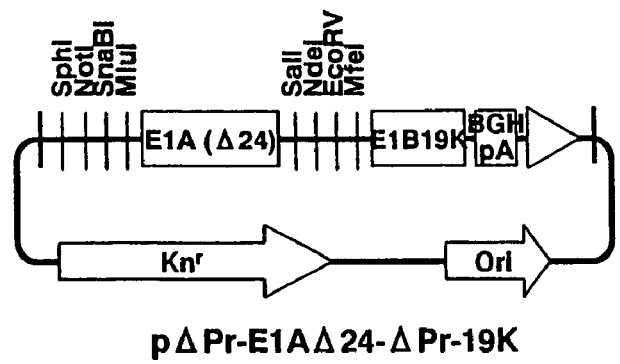
pΔPr-E1AΔ24-ΔPr-19K
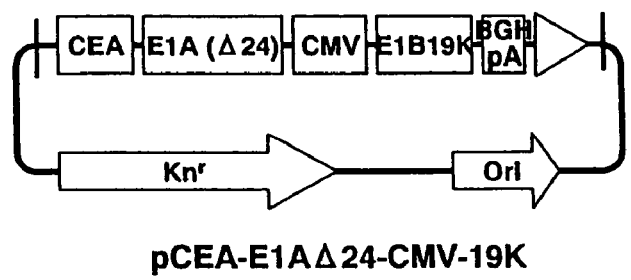
pCEA-E1AΔ24-CMV-19K
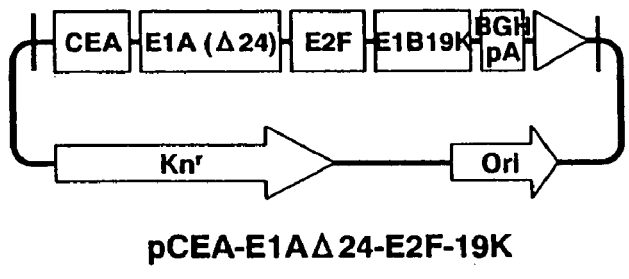
pCEA-E1AΔ24-E2F-19K
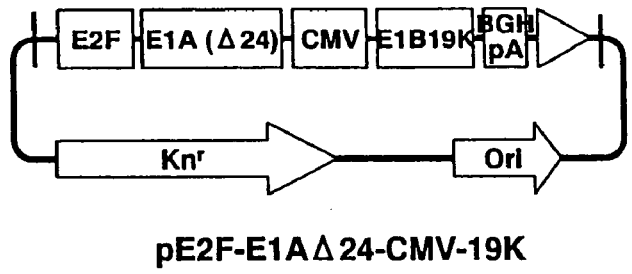
pE2F-E1AΔ24-CMV-19K
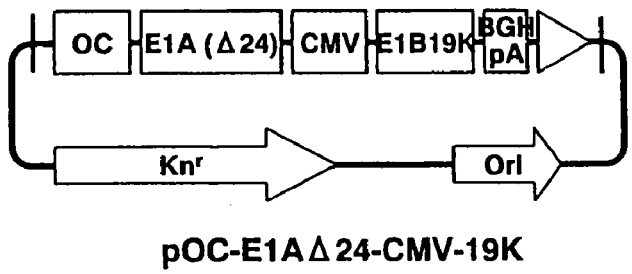
pOC-E1AΔ24-CMV-19K
Fig. 7

Vector plasmid having a therapeutic gene-expressing unit
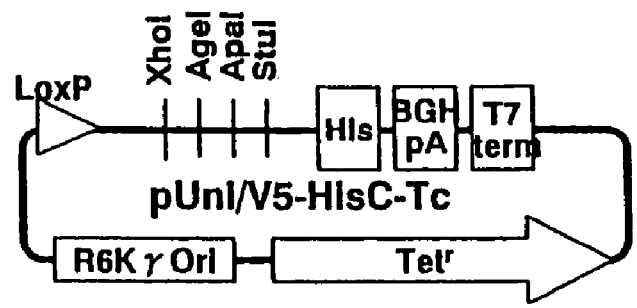
First therapeutic gene-expressing vector plasmid
(having an integrated constitutive high-expression promoter)
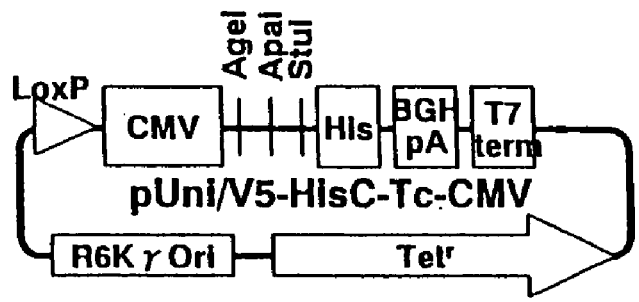
First therapeutic gene-expressing vector plası
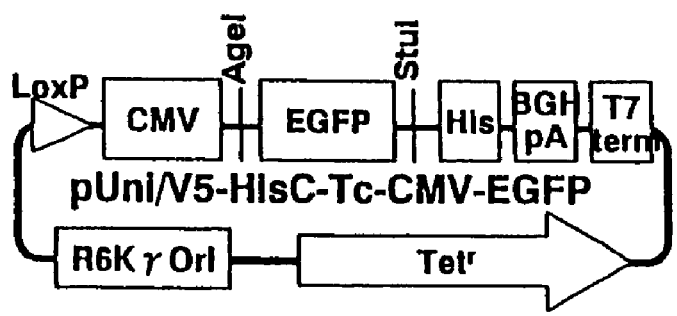
Fig. 8

SEQUENCE LISTING

<160> NUMBER OF SEQ ID NOS: 16

<210> SEQ ID NO 1
<211> LENGTH: 56
<212> TYPE: DNA
<213> ORGANISM: Artificial Sequence
<220> FEATURE:
<223> OTHER INFORMATION: PCR primer

<400> SEQUENCE: 1
tcagtcgcat gcgcggccgc tacgtaacgc gttacccggt gagttcctca agaggc        56

<210> SEQ ID NO 2
<211> LENGTH: 42
<212> TYPE: DNA
<213> ORGANISM: Artificial Sequence
<220> FEATURE:
<223> OTHER INFORMATION: PCR primer

<400> SEQUENCE: 2
ggacgtccta gggtcgacgc cccatttaac acgccatgca ag                        42

<210> SEQ ID NO 3
<211> LENGTH: 60
<212> TYPE: DNA
<213> ORGANISM: Artificial Sequence
<220> FEATURE:
<223> OTHER INFORMATION: PCR primer

<400> SEQUENCE: 3 tcagtccta gggtcgacca tatggatatc caattgcgtg ggctaatctt ggttacatct      60

-continued

```
<210> SEQ ID NO 4
<211> LENGTH: 36
<212> TYPE: DNA
<213> ORGANISM: Artificial Sequence
<220> FEATURE:
<223> OTHER INFORMATION: PCR primer

<400> SEQUENCE: 4
ggacgtggat ccgcgtctca gttctggata cagttc                              36

<210> SEQ ID NO 5
<211> LENGTH: 36
<212> TYPE: DNA
<213> ORGANISM: Artificial Sequence
<220> FEATURE:
<223> OTHER INFORMATION: PCR primer

<400> SEQUENCE: 5
tcagtcggat ccgcatgcat ctagagctcg ctgatc                              36

<210> SEQ ID NO 6
<211> LENGTH: 70
<212> TYPE: DNA
<213> ORGANISM: Artificial Sequence
<220> FEATURE:
<223> OTHER INFORMATION: PCR primer

<400> SEQUENCE: 6
ggacgtgaat tcataacttc gtataatgta tgctatatga ggtaattcag aagccataga    60
gcccaccgca                                                           70

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
ttgtaccgga ggtgatcgat ccacccagt                                      29

<210> SEQ ID NO 8
<211> LENGTH: 30
<212> TYPE: DNA
<213> ORGANISM: Artificial Sequence
<220> FEATURE:
<223> OTHER INFORMATION: PCR primer

<400> SEQUENCE: 8
tcctcgtcgt cactgggtgg atcgatcacc                                     30

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
ataaatggag cgaagaaacc                                                20

<210> SEQ ID NO 10
<211> LENGTH: 70
<212> TYPE: DNA
<213> ORGANISM: Artificial Sequence
<220> FEATURE:
```

<223> OTHER INFORMATION: PCR primer

<400> SEQUENCE: 10
ggacgtgaat tcataacttc gtataatgta tgctatatga ggtaatcttg atccaaatcc      60
aaacagagtc                                                             70

<210> SEQ ID NO 11
<211> LENGTH: 32
<212> TYPE: DNA
<213> ORGANISM: Artificial Sequence
<220> FEATURE:
<223> OTHER INFORMATION: PCR primer

<400> SEQUENCE: 11
tcagtcgtcg accgttgaca ttgattattg ac                                    32

<210> SEQ ID NO 12
<211> LENGTH: 32
<212> TYPE: DNA
<213> ORGANISM: Artificial Sequence
<220> FEATURE:
<223> OTHER INFORMATION: PCR primer

<400> SEQUENCE: 12
ggacgtcaat tggcttgggt ctccctatag tg                                    32

<210> SEQ ID NO 13
<211> LENGTH: 34
<212> TYPE: DNA
<213> ORGANISM: Artificial Sequence
<220> FEATURE:
<223> OTHER INFORMATION: PCR primer

<400> SEQUENCE: 13
tcagtcgcgg ccgcatcatc ccaccttccc agag                                  34

<210> SEQ ID NO 14
<211> LENGTH: 31
<212> TYPE: DNA
<213> ORGANISM: Artificial Sequence
<220> FEATURE:
<223> OTHER INFORMATION: PCR primer

<400> SEQUENCE: 14
ggacgtacgc gtccaggtct ctgctgtctg c                                     31

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
ctgcagggtc aggaggagaa                                                  20

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
gcgctgggct gctgctcagg                                                  20

METHOD OF PREPARING A PROLIFERATION-REGULATED RECOMBINANT ADENOVIRAL VECTOR EFFICIENTLY AND KIT FOR PREPARING THE SAME

CROSS-REFERENCE TO RELATED APPLICATIONS

This application is the National Stage of International Application No. PCT/JP2004/010998, filed Jul. 26, 2004, which claims the benefit of Japanese Patent Application Serial No. 2003-283427, filed on Jul. 31, 2003. The contents of both of the foregoing applications are hereby incorporated by reference in their entity.

TECHNICAL FIELD

The present invention relates to a method of rapidly and easily preparing a multifactorial proliferation-regulated recombination adenoviral vector for use in gene therapy and the studies thereof that proliferates specifically in a target organ and introduces a therapeutic gene specifically in the target organ, and a kit for preparing the same

BACKGROUND ART

Currently, the primary cause of death in Japan is cancer. In particular, it is quite difficult to prevent cancer metastasis completely with preexisting operational therapy, chemotherapy, or radiation therapy; thus, there is a need for research on newer therapies; and in particular, gene therapy is attracting attention and intensively studied. Based on basic studies, clinical tests on cancer gene therapy have been practiced frequently over past decades or so mainly in the United States as well as in Japan and other advanced countries, and the number of such patients is increasing year by year. However, there is no report that a patient was cured completely by the gene therapy. The biggest cause thereof is that most of the gene-introducing vectors currently used are nonproliferating viral vectors designed only to introduce a therapeutic gene after viral infection and not to proliferate, from the genetic engineering point of view, for safety. The nonproliferating viral vectors are indeed safer, but such a viral vector does not, of course, introduce the gene into the regions other than those into which the liquid containing the vector penetrates by in-vivo administration in actual clinical settings, even if the viral vector shows an excellent transferring efficiency in an in-vitro test using cultured cell. When a nonproliferating vector is used, it is not possible to overcome the problem of the recurrence of cancer from cancer cells in the organs where no gene is introduced, and that is the biggest cause for the gene therapy not giving expected clinical results.

There is a report of a variant adenovirus (ADV) that lacks a region in E1B that proliferates specifically in a p53 function-deficient cancer cell, which is often in the incompetent state, as an adenoviral vector (hereinafter, referred to as ADV) overcoming such a problem (Bischoff J. R., et all., Science. 1996 Oct. 18; 274 (5286): 373-376). Since then, such proliferation-regulated viral vectors, which proliferate specifically in cancer cell and do not proliferated in normal cell, have been studied. For example, an attempt was made to proliferate an adenovirus specifically in prostatic cancer cells by expressing the adenoviral E1A gene with a prostatic cancer-specific PSA promoter (Rodruguez, R., et al., Cancer Res, 57, 2559-2563, 1997).

However, proliferation-regulated viral vectors hitherto reported were designed to be regulated by a single factor, or the vectors were designed to proliferate only in cancer cells in response to a single factor by using the difference in expression of the factor in cancer cells and normal cells, to make the vectors specific to cancer. However, the difference between cancer and normal cells is not specified definitely only by a single factor, and thus, conventional proliferation-regulated viral vectors were far from specifically targeted to cancer. It would be necessary to use multiple factors different in properties simultaneously, to make the vector more specifically targeted to cancer, but there is no such a report so far. In addition, each of the traditional proliferation-regulated viral vectors should be prepared one by one separately in gene recombination. Adenovirus is a long DNA virus of 36 kB in length and thus, there are many restrictions in gene recombination thereof; for example, the number of the restriction enzymes for use in recombination of a plasmid vector containing the same is limited; and thus, it was impossible to perform the recombination efficiently. Thus, it was technically impossible to produce great amounts of proliferation-regulated adenoviral vectors rapidly and to prepare and evaluate a lot of proliferation-regulated viral vectors rapidly for use in screening vectors specifically targeted to cancer.

DISCLOSURE OF THE INVENTION

The present invention provides a new method of preparing a multifactorial proliferation-regulated recombinant adenoviral vector specifically targeted to cancer or the like efficiently, rapidly and easily, for use in screening and preparing viral vectors that are completely targeted to and proliferated in organs such as cancer, and a kit for preparing the same.

The present invention provides a method of preparing a proliferation-regulated recombinant adenoviral vector effectively, characterized by preparing a proliferation-regulated vector plasmid by preparing a restriction enzyme-recognizing unit in a vector plasmid having a proliferation-regulating unit and having an E1A region, at least one protein-coding region in a E1B region or the entire E1B region, a poly(A) signal sequence, and a recombinase-recognizing sequence in that order from upstream, by deleting both an endogenous promoter in the E1A region and an endogenous promoter regulating expression of the protein-coding gene at least in one protein-coding region of the E1B region and inserting restriction enzyme-recognizing sequences respectively in these deficient sites, and introducing a promoter expressing specifically in a target organ in each of the restriction enzyme-recognizing sequences; and additionally, integrating the proliferation-regulated vector plasmid into a vector plasmid having a adenoviral genome prepared by deleting the E1 region. The organ in the target organ include cell.

The present invention also provides a method of preparing a proliferation-regulated recombinant, adenoviral vector having an integrated therapeutic gene efficiently, comprising the steps of: preparing a second therapeutic gene-expressing vector plasmid by allowing a recombinase to react with the proliferation-regulated vector plasmid and a first therapeutic gene-expressing vector plasmid prepared by inserting a constitutive high-expression promoter or a therapeutic gene-expressing promoter and a therapeutic gene in that order from upstream into the restriction enzyme-recognizing sequence of the vector plasmid containing a therapeutic gene-expressing unit, which is prepared by inserting a recombinase-recognizing sequence and a restriction enzyme-recognizing sequence respectively in that order from upstream; and additionally, integrating the second therapeutic gene-expressing vector plasmid into a vector plasmid having an adenoviral genome prepared by deleting the E1 region.

The present invention also provides a method of preparing a proliferation-regulated recombinant, adenoviral vector having an integrated therapeutic gene efficiently, comprising the steps of: allowing a recombinase to react with the proliferation-regulated adenoviral vector plasmid, and the first therapeutic gene-expressing vector plasmid prepared by inserting a constitutive high-expression promoter or a therapeutic gene-expressing promoter and a therapeutic gene in that order from upstream to the restriction enzyme-recognizing sequence of the vector plasmid having a therapeutic gene-expressing units prepared by inserting a recombinase-recognizing sequence and a restriction enzyme-recognizing sequence respectively in that order from upstream.

The present invention also provides a vector plasmid having a proliferation-regulating unit, for use in the method of preparing a proliferation-regulated recombinant adenoviral vector efficiently. The vector plasmid having a proliferation-regulating unit allows easy preparation of a proliferation-regulated vector plasmid as well as a proliferation-regulated recombinant adenoviral vector by introducing arbitrary two or more promoters expressing specifically in a target organ to the respective restriction enzyme-recognizing sequences.

The present invention also provides a preparative kit having a vector plasmid having a proliferation-regulating unit and a vector plasmid having an E1 region-deficient adenoviral genome, for use in the method of preparing a proliferation-regulated recombinant adenoviral vector efficiently. The preparative kit allows easy preparation of a proliferation-regulated recombination adenoviral vector proliferating only in the target organ with its arbitrary two or more promoters expressing specifically in the target organ.

The present invention also provides a vector plasmid containing a therapeutic gene-expressing unit, for use in the method of preparing a proliferation-regulated recombinant adenoviral vector having an integrated therapeutic gene efficiently. The vector plasmid having a therapeutic gene-expressing unit allows easy preparation of a first therapeutic gene-expressing vector plasmid as well as a proliferation-regulated recombinant adenoviral vector by introducing an arbitrary therapeutic gene expressing in a target organ into a restriction enzyme-recognizing sequence.

The present invention also provides a preparative kit, including a vector plasmid having a proliferation-regulating unit, a vector plasmid having a therapeutic gene-expressing unit, and a vector plasmid having an adenoviral genome at least lacking the E1A region, for use in the method of preparing a proliferation-regulated recombinant adenoviral vector having an integrated therapeutic gene efficiently. The preparative a kit allows easy preparation of a proliferation-regulated recombinant adenoviral vector proliferating only in a target organ, having arbitrary two or more promoters expressing specifically in a target organ and an arbitrary therapeutic gene expressing in a target organ.

The present invention also provides a treatment method for various diseases including malignant tumors, wherein the proliferation-regulated recombinant adenoviral vector prepared by any one of the methods above is utilized.

Examples of the adenoviruses for use in the present invention include human adenovirus type 5, human adenovirus type 2, other types of human adenoviruses, adenoviruses of other animal species, and the like.

The vector plasmid having a proliferation-regulating unit can be prepared by using a general method in genetic engineering as follows:

An E1A region including a poly(A) signal sequence but containing no endogenous promoter is amplified by PCR, while using an adenoviral plasmid at least containing a 5'-side genome as the template; and the PCR products obtained and a cloning vector are digested with a restriction enzyme and ligated into a cloning vector, to give pΔPr.E1A (hereinafter, Pr is a promoter). An arbitrary restriction enzyme-recognizing sequence is inserted into the sense primer and the anti-antisense primer of PCR, and the arbitrary restriction enzyme-recognizing sequence is inserted into the endogenous promoter-deficient site. The template plasmid is not particularly limited, if it contains at least an adenoviral 5'-side genome. The cloning vector is also not particularly limited.

Then, similarly to above at least one protein-coding region of the E1B having no endogenous promoter regulating expression of the protein-coding genes in the protein-coding region is amplified by PCR by using a plasmid containing an adenoviral genome as the template; and the PCR products and the pΔPr.E1A are digested with a restriction enzyme and ligated into pΔPr.E1A, to give pΔPr.E1A-ΔPr.XkΔpA (hereinafter, pA means a poly(A) signal sequence). XK represents at least one protein-coding region coding some proteins such as X55KDa and 19KDa in the E1B region.

Similarly to above it is amplified by PCR by using a plasmid containing a poly(A) signal sequence as the template; and the PCR products obtained is digested with pΔPr.E1A-ΔPr.XkΔpA with a restriction enzyme and ligated into pΔPr.E1A-ΔPr.XkΔpA, to give pΔPr.E1A-ΔPr.XKpA. A recombinase-recognizing sequence is inserted into the PCR primer, and inserted into downstream of the poly(A) signal sequence. The plasmid containing a poly(A) signal sequence is not particularly limited.

The vector plasmid having a proliferation-regulating unit pΔPr.E1A-ΔPr.XKΔpA thus obtained has no endogenous promoter in the E1A region and no endogenous promoter regulating expression of the protein-coding genes in the protein-coding region of E1B region, and a restriction enzyme-recognizing sequences are inserted to these deficient sites. The restriction enzyme-recognizing sequence preferably has a site for a restriction enzyme that digests its blunt end such as SnaBI, EcoRV, HaeIII, AluI, or SmaI.

Because there is a report that a variant adenovirus lacking Rb protein-binding sequence (923 to 947 bp, 24 bp) in the E1A region proliferates specifically in tumor cells (Heise, C. et al., Nat. Med. 2000; 6(10): 1134-9), the Rb protein-binding sequence in the E1A region may be deleted. The Rb protein-binding sequence-deficient E1AΔ24 is obtained by mutagenesis of the E1A region by a mutagenic method using PCR, specifically by using a primer designed from the Rb protein-binding sequence by using the adenoviral plasmid above at least containing a 5'-side genome as the template and (Current Protocols in Molecular Biology, John Wiley & Sons, Inc., 8.5.7 to 8.5.9, 1999). E1AΔ24 and the vector plasmid having a proliferation-regulating unit pΔPr.E1A-ΔPr.XkpA are digested with a restriction enzyme and then ligated, to give a Rb protein-binding sequence-deficient vector plasmid having a proliferation-regulating unit pΔPr.E1AΔ24-ΔPr.XKpA.

The recombinase-recognizing sequence is a base sequence recognized by recombinase, a specific DNA-recombination enzyme, and is also a base sequence that causes DNA-recombination reactions such as cleavage, substitution, and binding of the DNA chain located between two recombinase-recognizing sequences recognized by the recombinase. The recombinase-expressing gene is a gene expressing a recombinase, and typical examples thereof include, but are not limited to, genes expressing a bacteriophage P1-devied recombinase Cre recognizing other mutant sequences such as recombinase-recognizing sequences LoxP and LoxH (Sternberg et al. J. Mol. Boil. Vol. 150, 467-486 (1981)), a yeast (*Saccharomyces cerevisiae*)-derived recombinase FLP recognizing recombinase-recognizing sequence FRT (Babineau et al., J. Biol. Chem. Vol. 260, 12313-12319 (1985)), and a *Zygosaccharomyces rouxii* pSR1 plasmid-derived R (Matsuzaki et al., Mol. Cell. Biol., Vol. 8, 955-962 (1988)), and the like.

In addition, a sequence having the E1B region in a vector plasmid containing a proliferation-regulating unit as the entire region of E1B, pΔPr.E1A-ΔPr.E1BpA, may also be used. It is amplified by PCR by using a primer designed based on the E1B base sequence and a plasmid at least containing a 5'-side genome of the adenovirus described above as the template, to give PCR products. The PCR products and the vector plasmid having a proliferation-regulating unit pΔPr.E1AΔ24-ΔPr.XKpA are digested with a restriction enzyme and then ligated, to give a vector plasmid having a proliferation-regulating unit pΔPr.E1A-ΔPr.E1BpA wherein E1BXK is replaced with the entire E1B sequence.

A proliferation-regulated vector plasmid can be prepared by inserting an organ-specific expressing promoter into the restriction enzyme-recognizing sequences inserted to the respective endogenous promoter-deficient sites in the vector plasmid having a proliferation-regulating unit prepared, pΔPr.E1A-ΔPr.XKpA.

Examples of the target organ-specific expressing promoters when the target organ is cancer cell include CEA (carcinoembryonic antigen) promoters expressing only in cancer cells (Mol. Cell. Biol., 10(6), 2738-2748, 1990), E2F promoter (Neuman, E., et al., Mol. Cell. Biol., 14(10) 6607-6615, 1994), OC (osteocalcin) promoter (Morrison, N. A., et al., Science, 246, 1158-1161,1989), FLK-1 promoter specific to malignant melanoma, fibrosarcoma, and others (Xie, B., et al., Br. J. Cancer, 81, 1335-1343, 1999), VEGF promoter specific to lung cancer and others (Koshikawa, N., et al., Cancer Res., 60, 2936-2941, 2000), c-Myc promoter specific to small cell lung cancer and others (Kumagai T., et al., Cancer Res., 354-358, 1996), SLPI promoter specific to lung cancer, ovarian cancer, and others (Garver, R I, et al., Gene Ther, 1, 46-50, 1994), PSA promoter specific to prostatic cancer (Latham, J P, et al. , Cancer Res, 60, 334-342, 2000) , tyrosinase promoter specific to malignancy melanoma and others (Vile, R G, et al., Cancer Res., 53, 962-967, 1993), AP-2 promoter specific to breast cancer (Pandha, H S, et al., J. Clin. Oncol., 17, 2180-2189, 1999), TERT promoter specific to brain tumor and many cancers (Takakura M, et al., Cancer Res., 59, 551-557, 1999), and the like.

It is possible to prepare a multifactorial proliferation-regulated adenoviral vector plasmid that proliferates only in target organs but not in other organs by regulation of the two organ-specific expressing promoters, by introducing the proliferation-regulated vector plasmid in a plasmid having an adenoviral genome prepared by deleting its E1 region. The proliferation-regulated adenoviral vector plasmid prepared can be transfected and proliferated in cell constitutively producing adenoviral E1-region proteins such as human fetal renal cell-derived 293 cell (Graham, F L, et al., J. Gen. Virol., 36 (1) : 59-74). Because substitution of the fiber governing adenoviral infection with a ligand expressed in cancer cell at high rate in the plasmid having an adenoviral genome prepared by deleting its E1 region allows cancer cell-specific targeting of the adenovirus, the fiber in the plasmid having an adenoviral genome prepared by deleting the E1 region may be substituted with such a ligand.

Alternatively, a vector plasmid containing a therapeutic gene-expressing unit can be prepared according to a general method in gene engineering as follows:

A plasmid having a constitutive high-expression promoter or an expression promoter regulating expression of the therapeutic gene and a restriction enzyme-recognizing sequence for integrating the therapeutic gene in downstream of LoxP or the variant sequence thereof is prepared.

If the drug tolerance gene in the vector plasmid containing a therapeutic gene-expressing unit and the drug tolerance gene in the vector plasmid having a proliferation-regulating unit are the same, it becomes possible to select only correct recombinant plasmids efficiently and easily, by modifying one of them to make the drug tolerance genes different from each other, and making Ori in the vector plasmid having a therapeutic gene-expressing unit duplicate only in competent cells expressing a pir gene such as R6Kγ.

A first therapeutic gene-expressing vector plasmid is prepared by inserting a constitutive high-expression promoter or a promoter expressing a therapeutic gene for treatment of targeted a organ such as cancer cell and the therapeutic gene in that order from upstream into the restriction enzyme-recognizing sequence in the vector plasmid containing a therapeutic gene-expressing unit prepared. The constitutive high-expression promoter is a promoter expressing most genes including the therapeutic gene strongly and constitutively, and examples thereof include CA promoter (hybrid promoter of cytomegalovirus enhancer and chicken β-actin promoter), CMV promoter (cytomegalovirus early-gene enhancer/promoter), and the like. The therapeutic gene is a gene treating a disease at the molecular level when introduced and expressed in a diseased organ, and examples thereof, for example for treatment of cancer, include cancer-suppressing genes such as P53 gene, cytokine genes such as IL-2, suicide genes such as HSV-tk gene, apoptosis-inducing genes such as Fas, antisense genes, and the like. Alternatively, the therapeutic gene-expressing promoter for is a promoter regulating expression of these therapeutic genes.

The proliferation-regulated vector plasmid and the first therapeutic gene-expressing vector plasmid recombine to each other in the presence of a recombinase, giving a second therapeutic gene-expressing vector plasmid having an introduced promoter expressing specifically in a target organ and a therapeutic gene expressing in the target organ. It is possible to prepare a proliferation-regulated adenovirus vector plasmid containing a therapeutic gene, by integrating the second therapeutic gene-expressing vector plasmid with the plasmid having an adenoviral genome prepared by deleting the E1 region.

It is also possible to prepare a proliferation-regulated adenoviral vector plasmid having a therapeutic gene, by mixing a proliferation-regulated adenoviral vector plasmid not having the therapeutic gene and the first therapeutic gene-expressing vector plasmid, treating with a recombinase, and allowing them to recombine. A proliferation-regulated adenoviral vector plasmid having a therapeutic gene may be prepared by allowing a recombinase to react with a proliferation-regulated adenoviral vector plasmid and the first therapeutic gene-expressing vector plasmid and then transforming these plasmids.

It is possible to prepare a proliferation-regulated recombinant adenoviral vector, by transfecting the proliferation-regulated adenoviral vector plasmid not containing a therapeutic gene or the proliferation-regulated adenoviral vector plasmid having a therapeutic gene thus prepared, to a cell constitutively expressing adenoviral E1-region proteins, such as human fetal renal cell-derived 293 cell.

Alternatively, a proliferation-regulated adenoviral vector plasmid may be prepared by cotransfecting the proliferation-regulated adenoviral vector plasmid not having the therapeutic gene and the first therapeutic gene-expressing vector plasmid to a recombinase-expressing cell. In such a case, it is possible to prepare the proliferation-regulated recombinant adenoviral vector having a therapeutic gene directly, by cotransfecting a cell expressing both recombinase and adenoviral E1-region proteins, for example 293 cell or the like, to a recombinase-expressing cell.

Proliferation, collection and purification of the proliferation-regulated recombination adenoviral vector not containing a therapeutic gene and the proliferation-regulated recombinant adenoviral vector having a therapeutic gene thus obtained may be performed according to a common method of handling adenoviral vectors, for example, by using a cell constitutively generating adenoviral E1-region proteins such as human fetal renal cell-derived 293 cell.

Hereinafter, the principle of the method of preparing a proliferation-regulated recombinant adenoviral vector efficiently according to the present invention will be described with reference to a drawing in FIG. 1 for clear-cut understanding, taking targeting to cancer cell as an example. In the Figure, (1) represents a promoter regulating expression of E1A; (2), a promoter regulating expression of E1B; (3), deficiency of Rb protein-binding domain; (4), deficiency of E1B55Da and/or E1B 19KDa; (5), a promoter regulating a therapeutic gene; (6), a therapeutic gene; and (7), modification of adenovirus structure protein gene.

It is possible to regulate proliferation specific to cancer, by introducing arbitrary cancer cell-specific expressing promoters in the regions (1) and (2) properly. E1A is a region first transcripted after infection of the adenovirus, and, if not, virus proliferation does not occur. On traditional nonproliferating adenoviral vectors, genes in the E1A region are deleted and desirable therapeutic genes are introduced instead. On the other hand, the E1B region, which codes some proteins such as 55KDa and 19KDa, is also transcripted in the early stage after transcription of E1A, and transcription and activation of the E1B region are also said to be important in viral proliferation. Thus, endogenous viral promoters in the regions E1A and E1B are removed and restriction enzyme-recognizing sequences (multicloning sites) are inserted in the regions for easier introduction of other promoters. It is possible then to make the adenovirus proliferate specifically to cancer, simply by introducing two different cancer cell-specific high-expression promoters.

In addition, there are some reports that it was possible to proliferate an adenovirus specifically to cancer by deleting the Rb protein-binding domain in the region (3) or E1B55KDa and/or E1B 19KDa regions in the region (4), although the mechanism is yet to be clear. It is possible to make the factors (3) and (4) as well as the factors (1) and (2) specifically targeted to cancer easily, by preparing plasmids both having and not having the regions (3) or (4). Thus, regulation of cancer-specific proliferation is made possible first by the four completely independent factors.

On the other hand, it is possible to make it more specifically targeted to cancer, by using cancer specific promoters, genes having a significant effect only on cancer, or the like respectively in the regions (5) and (6).

The region (7) is a region for easier modification of the adenoviral structure protein-coding genes such as fibers in the adenovirus plasmid vector having an adenoviral genome.

The present invention is characterized in that it is possible to perform gene recombination for preparation of a desirable proliferation-regulated recombinant adenoviral vector extremely efficiently and freely, by using three independent plasmid vectors, a plasmid having a proliferation-regulating unit, a vector plasmid having a therapeutic gene-expressing unit, and a plasmid having an adenoviral genome lacking the E1A region. That is, it is possible to prepare these three plasmids independently by recombination, integrate and insert these plasmids easily among them, and combine the respective factors freely and rapidly. Such advantages are obtained by the following methods:

(a) It is possible to select desirable correct recombinant plasmids effectively, by changing the replication origin on a plasmid with that functioning only in special *E. coli* and making the most of the difference between the antibiotic-resistance genes. (b) It is possible to introduce a therapeutic gene into an adenoviral vector easily, by using a recombination reaction in *E. coli* or a 293 cell in preparation of adenovirus. (c) It is possible to insert a vector plasmid having a proliferation-regulating unit or a recombinant plasmid having a proliferation-regulating unit and a therapeutic gene-expressing unit into a plasmid containing an adenoviral genome freely in ligation by using its restriction enzyme sites. Thus in this manner, it is possible to select and integrate three kinds of desirable plasmids and prepare a proliferation-regulated recombinant adenoviral vector in a desirable combination easily according to its applications. It is also easy to modify the adenoviral vector plasmid after preparation.

A shuttle vector may be used as the vector according to the present invention.

BRIEF DESCRIPTION OF THE DRAWINGS

FIG. 1 is a schematic view illustrating the principle of the method of preparing a proliferation-regulated recombinant adenoviral vector efficiently according to the present invention.

FIG. 2 is a table showing the PCR primers and the condition of the PCR reaction used in preparation of the vector plasmid having a proliferation-regulating unit of Example 1.

FIG. 4 is a table showing the PCR primers and the condition of the PCR reactions used in preparation of the vector plasmid having a proliferation-regulating unit but lacking the Rb protein-binding sequence in Example 1 and the vector plasmid containing the entire E1B region and a proliferation-regulating unit.

FIG. 5 is a table showing the PCR primer used in preparation of the vector plasmid for proliferation regulation in Example 2 and the condition of the PCR reaction.

FIG. 6 is a figure showing proliferation-regulated vector plasmids having a Rb protein binding site prepared in Example 2.

FIG. 7 is a figure showing the proliferation-regulated vector plasmids lacking a Rb protein binding site prepared in Example 2.

FIG. 8 is a figure showing the vector plasmid having a therapeutic gene-expressing unit prepared in Example 3 and the first therapeutic gene-expressing vector plasmid prepared in Example 4.

BEST MODE FOR CARRYING OUT THE INVENTION

Figure 3:
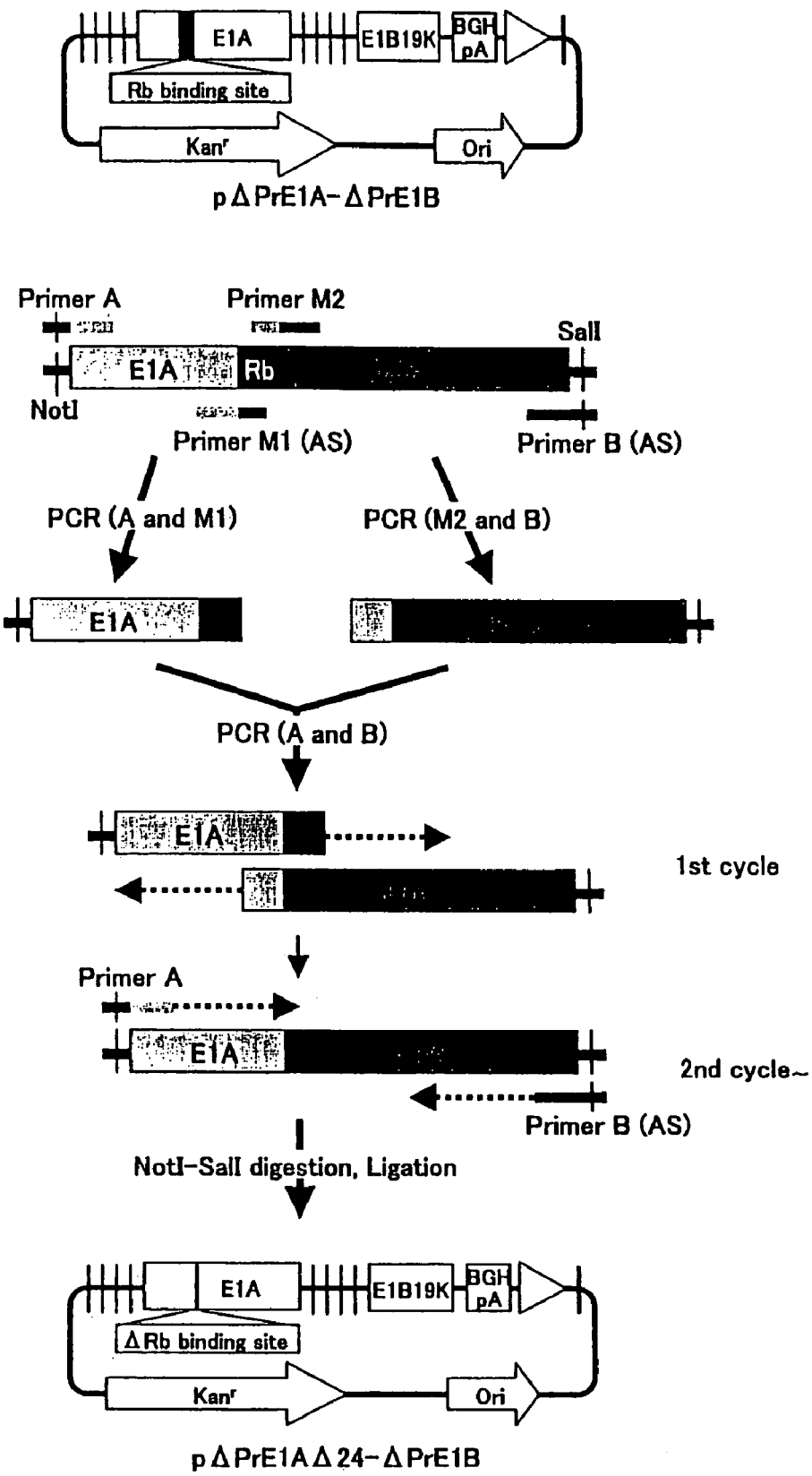
FIG. 3 is an explanatory drawing showing the principle of the mutagenic method used in preparation of the vector plasmid having a proliferation-regulating unit lacking the Rb protein-binding sequence obtained in Example 1.

Hereinafter, the present invention will be described in detail with reference to Examples.

Example 1

(Preparation of a Vector Plasmid Having a Proliferation-regulating Unit for Expression of the Adenoviral E1 Region with an Arbitrary Promoter)

The plasmid vector used in preparing the adenoviral vector was pHM5. pHM5 was a cloning vector having restriction enzyme sequences of SphI, PstI, HincII, XbaI, BamHI, KpnI, SacI, and EcoRI, which was provided from by Dr. Mark A. Kay (Stanford University) (see for details in Human Gene Therapy, 10: 2013-2017, 1999). The plasmid pXC1 containing a human type-5 adenoviral genome 5'-sequence was purchased from Microbix (Toronto, Canada). The region from the adenovirus genomic E1A protein-coding region to the polyadenylation signal containing no endogenous promoter (474 to 1658 bp) and the region only containing E1B 19KDa protein-coding region (1684 to 2285 bp) but not containing an endogenous promoter or a polyadenylation signal are amplified and cloned, by using pXC1 as the template and the Bovine growth hormone polyadenylation signal sequence (BGHp: bovine growth factor polyadenylation signal sequence), pRC/RSV (Invitrogen, catalogue No.: A-150307) as the template, by PCR using KOD DNA polymerase (Toyobo, catalogue No.: KOD-101), while using the primer set shown in FIG. 2. The E1A sense primer (S-E1A, sequence No. 1) used had added restriction enzyme-recognizing sequences of SphI, NotI, SnaBI, and MluI; the E1A antisense primer (AS-E1A, sequence No. 2), SalI and AvrII-recognizing sequences; the E1B 19KDa sense primer (S-E1B19K, sequence No. 3), restriction enzyme-recognizing sequences of AvrII, SalI, NdeI, EcoRV, and MfeI; the E1A antisense primer (AS-E1B19K, sequence No. 4), BamHI-recognizing sequence; the BGHpA sense primer (S-BGHpA, sequence No. 5), BamHI-recognizing sequence; and the E1A antisense primer (AS-BGHpA, sequence No. 6), 34 bp LoxH sequence and EcoRI-recognizing sequence; (see FIG. 2 for the sequences of respective primers and the PCR condition). Then, the PCR products of the E1A coding region thus obtained and pHM5 are digested with restriction enzymes SphI (Takara Shuzo, catalogue No.: 1180A) and SalI (Toyobo, catalogue No.: SAL-111), and ligated with T4 DNA ligase (Takara Shuzo, catalogue No.: 6022), to give a plasmid pΔPr.E1A having the E1A coding region in pHM5. Separately, the PCR products containing the E1B19K coding region obtained above and pΔPr.E1A were digested with SalI and BamHI (Toyobo, catalogue No.: BAH-111) and ligated with T4 DNA ligase, to give a plasmid pΔPr.E1A-ΔPr.19KΔpA.

Further, BGHpA, the PCR product obtained above, and pΔPr.E1A-ΔPr19KΔpA were digested with BamHI and EcoRI (Toyobo, catalogue No.: ER0271) and ligated, to give a plasmid pΔPr.E1A-ΔPr.19K-BGHpA (hereinafter, referred to as pΔPr.E1A-ΔPr.19 K, as BGHpA is omitted). For elimination of a possibility of variation in base sequential that may occur during cloning by PCR, the fact that the DNA sequence of pΔPr.E1A-ΔPr.19K was correct and a desirable DNA was prepared was confirmed by using a DNA sequencer (ABI PRISM 310 Genetic Analyzer, manufactured by Applied Biosystems). All DNA's cloned by PCR hereinafter were also confirmed similarly by using the DNA sequencer.

The plasmid pΔPr.E1A-ΔPr.19K thus prepared was a plasmid having a background of pHM5 and has, from upstream, a multicloning site containing restriction enzyme-recognizing sequences of SphI, NotI, SnaBI, and MluI, an E1A protein-coding region, a multicloning site containing restriction enzyme-recognizing sequences of SalI, NdeI, EcoRV, and MfeI, an E1B 19KD protein-coding region, and the BGHpA and LoxH sequences.

Accordingly, it is possible to insert promoters freely in the upstream region by using the upstream multicloning sites of E1A and E1B191KDa. In addition, the upstream multicloning sites of E1A and E1B 19KDa have at least one restriction enzyme site giving a blunt end, SnaBI or EcoRV, and thus, it is possible to integrate a promoter sequence digested by any restriction enzyme into the vector plasmid having a proliferation-regulating unit pΔPr.E1A-ΔPr.19K easily and reliably, if it is ligated after blunt end processing.

For preparation of a variant E1A lacking the Rb protein-binding sequence, mutagenesis by PCR using pXC1 shown in FIG. 3 as the template (Current Protocols in Molecular Biology, John Wiley & Sons, Inc., 8.5.7 to 8.5.9, 1999) was performed as described below, to delete the pXC1 923 to 947-bp region corresponding to the Rb protein-binding sequence. First, PCR by using the sense primer having restriction enzyme-recognizing sequences SphI, NotI, SnaBI, and MluI inserted in the E1A 5'-terminal sequence (S-E1A, sequence No. 1) used in E1A cloning and an antisense primer having 10-bp (913 to 922 bp) and 20-bp (947 to 366) sequences added immediately before and after the Rb-binding sequence AS-Δ24 (sequence No. 8) and also by using a sense primer having 20-bp (903 to 922 bp) and 10-hp (947 to 956) sequences added immediately before and after the Rb-binding sequence Δ24 (sequence No. 7) and an antisense primer having a restriction enzyme SalI-recognizing sequence inserted at the E1A 3' terminal (AS-E1A, sequence No. 2) was performed as the first PCR, to give respectively PCR products of 475 bp and 726 bp. Both of the PCR products were combined and subjected to second PCR by using a sense primer S-E1A and an antisense primer AS-E1A as the templates, to give a bound product, i.e., E1A lacking the Rb protein-binding sequence (24 bp) (referred to as E1AΔ24). The primer sequences and the condition of the PCR reaction are shown in FIG. 4. The E1AΔ24 was digested with restriction enzymes SphI and SalI (Toyobo, catalogue No.: SAL-111) into pΔPr.E1A-ΔPr.19K, which was then inserted with a DNA ligase (Takara Shuzo, catalogue No.: 6022) into wild type E1A, to give pΔPr.E1AΔ24-ΔPr.19K. Thus, pΔPr.E1AΔ24-ΔPr.10K was a vector plasmid having a proliferation-regulating unit having a similar base sequence and structure, except that the Rb protein-binding sequence in E1A was removed from pΔPr.E1A-ΔPr.19K.

A shuttle vector having not only an E1B gene 19-KDa protein region but also the entire E1B sequence including 55KDa and other regions of wild type adenovirus was prepared in the following manner: First, a sense primer having the same sequence as that of the 20-bp region from 14 bp to 33 bp upstream of the KpnI-recognizing sequence in E1B (2015 to 2034 bp in pXC1) (S-E1B-2015, sequence No. 9) and an antisense primer having the LoxH sequence (34 bp) and the EcoRI-recognizing sequence inserted in the sequence of 24 bp (4050 to 4073 bp in pXc1) from the polyadenylation signal sequence 3' terminal of wild type E1B (As-E1B-4073, sequence No. 10) were amplified by BCR, by using KOD DNA polymerase (Toyobo, catalogue No.: KOD-101) and pXC1 as the template, while cloning the region of 2015 to 4073 bp in E1B. The primer sequences and the PCR reaction condition are summarized in FIG. 4. The PCR products were digested with a restriction enzymes KpnI (Toyobo, catalogue No.: KPN-111) and EcoRI (Toyobo, catalogue No.: ECO-111), and inserted with a DNA ligase (Takara Shuzo, catalogue No.: 6022) into the digestion product of pΔPr.E1A-ΔPr.19K digested similarly with KpnI and EcoRI. Thus, E1B19K and the entire E1B sequence were replaced, and the plasmid obtained was designated as pΔPr.E1A-ΔPr.E1B. pΔPr.E1A-ΔPr.E1B thus prepared is a plasmid allowing expression by external promoters respectively having entire proteins of E1A and E1B, and having a base sequence and a structure similar to those of pΔPr.E1A-ΔPr.19K, except that the E1B 19-KDa region in pΔPr.E1A-ΔPr.E1B is the entire E1B coding region. A vector plasmid having a proliferation-regulating unit containing the entire E1B sequence pΔPr.E1AΔ24-ΔPr.E1B was obtained from the pΔPr.E1AΔ24-ΔPr.19K lacking the Rb protein-binding sequence in E1A in a similar manner.

Example 2

(Insertion of an Arbitrary promoter Into a Vector Plasmid Having a Proliferation-regulating Unit and Preparation of a Proliferation-regulated Vector Plasmid)

Examples of experiments inserting an arbitrary desirable promoter into the vector plasmid having a proliferation-regulating unit obtained above will be described below. First, a plasmid having a CMV (Cytomegalovirus) promoter (Boshart, M., et al., Cell, 41, 52101-530, 1985, Nelson, J. A., et al., Mol. Cell. Biol., 7, 4125-4129, 1987) inserted at a position upstream of E1B19K was prepared. The CMV promoter was amplified by PCR, by using a plasmid pRC/CMV (Invitrogen, catalogue No.: A-150307) as the template, a sense primer having a SalI recognition site (S-CMVp, sequence No. 11), and an antisense primer having an MfeI recognition site (AS-CMVp, sequence No. 12) (see FIG. 5 for the sequences of respective primers and the condition of PCR). The PCR products (pRC/CMV φ231 to 893), plasmids pΔPr.E1A-ΔPr.19K and pΔPr.E1AΔ24-ΔPr.19K, were digested with SalI (Toyobo, catalogue No.: SAL-111) and MfeI (New England Biolabs, catalogue No.: R0589s) and ligated with T4 DNA ligase while inserting the CMV promoter into the upstream region of E1B19K, to give proliferation-regulated vector plasmids pΔPr.E1A-CMV-19K and pΔPr.E1AΔ24-CMV-19K respectively.

Then, a CEA promoter was inserted into the upstream region of E1A respectively of pΔPr.E1A-CMV-19K and pΔPr.E1AΔ24-CMV-19K. First, 10 μl (5.6×10$^{10}$ pfu/μl) of adenovirus AxCEAprTK having the CEA promoter (provided from by the DNA Bank of Riken Institute of Physical and Chemical Research) was mixed with 10 μl of 10% SDS (Sodium dodecylsulfate, Wako Pure Chemical Industries, catalogue No.: 199-07145), 8 μl of 0.5M EDTA (Ethylenediaminetetraacetic acid, Wako Pure Chemical Industries, catalogue No.: 311-90075), and 170.75 μl of distilled water, and the mixture was stirred well. 1.25 μl of 20% proteinase K (Roche Diagnostics GmbH, catalogue No.: 745725) was added additionally; the mixture was allowed to be digested at 56° C. for 2 hours; and the products were subjected to phenol-chloroform purification and ethanol precipitation, to give 2 μg of a genome DNA AxCEAprTK. A region of 424 bp to 2 bp upstream of the CEA coding a regional initiation codon (Osaki, T., et al., Cancer Res., 54, 5258-5261) was amplified by PCR by using the DNA as the template, a sense primer having a restriction enzyme NotI-recognizing sequence (S-CEAp, sequence No.: 13), and an antisense primer having a restriction enzyme MluI-recognizing sequence (AS-CEAp, sequence No. 14) (see FIG. 5 for the sequences of respective primers and the PCR condition). The PCR products were digested with MluI (Toyobo, catalogue No.: MLU-101) and NotI (Toyobo, catalogue No.: NOT-111). pΔPr.E1A-CMV-19K and pΔPr.E1AΔ24-CMV-19K digested with MluI and NotI similarly were ligated with T4 DNA ligase, to give respectively pCEA-E1A-CMV-19K and pCEA-E1AΔ24-CMV-19K. The pCEA-E1A-CMV-19K and the pCEA-E1AΔ24-CMV-19K thus prepared are proliferation-regulated vector plasmids expressing respectively E1A and E1AΔ24 by a CEA promoter and E1B19K by a CMV promoter (see FIGS. 6 and 7).

Then, a construct having inserted E2F promoters respectively as the E1A and E1319K promoters was prepared. The E2F promoter was prepared by cleaving the plasmid pABS.4: E2F-GFP provided from by Dr. Fine, H. (National Cancer Institute, Bethesda, Md.) with restriction enzymes SpeI (Toyobo, catalogue No.: SPE-101) and XhoI (Toyobo, catalogue No.: XHO-101) and blunting with T4 DNA polymerase (NMBI, catalogue No.: EP0061). The pΔPr.E1A-CMV-19K and pΔPr.E1AΔ24-CMV-19K above were digested with SalI, blunted with T4 DNA polymerase, dephosphorylated with a calf intestine alkaliphosphatase (CIP: calf small-intestine alkaline phosphatase, Takara Shuzo, catalogue No.: 2250A) for prevention of autoligation, and ligated to the cleaved E2F promoter with T4 DNA ligase, to give pE2F-E1A-CMV-19K and pE2F-E1AΔ24-CMV-19K respectively. The PE2F-E1A-CMV-19K and pE2F-E1AΔ24-CMV-19K thus prepared were proliferation-regulated vector plasmids expressing E1A or E1AΔ24 by an E2F promoter and E1B19K by a CMV promoter (see FIGS. 6 and 7).

By a similar method, the CMV promoter regions of pCEA-E1A-CMV-19K and pCEA-E1AΔ24-CMV-19K were removed by digestion with SalI and MfeI, the remaining vector regions were treated with T4 DNA polymerase and CIP, and ligated with the cleaved E2f promoter with T4 DNA ligase, to give respectively plasmids of pCEA-E1A-E2F-19K and pCEA-E1AΔ24-E2F-19K. The pCEA-E1A-E2F-19K and pCEA-E1AΔ24-E2F-19K thus prepared were proliferation-regulated vector plasmids expressing E1A or E1AΔ24 by a CEA promoter and E1319K by an E2F promoter (see FIGS. 6 and 7).

Then, a construct having an OC (osteocalcin) promoter inserted as the E1A promoter was prepared. First, 5×10$^5$ human osteosarcoma cells SaOS-2 (provided from the Cell Research Center for Biomedical Research, Institute of Development, Aging and Cancer, Tohoku University) were treated with trypsin and collected; the region 834-bp upstream to 34-bp downstream of the transcription initiation site was amplified by PCR by using SepaGene (Sanko Junyaku catalogue No.: SG0025), the DNA collected from SaOS-2 as the template, and an ExTaqI DNA polymerase (Takara Shuzo, catalogue No.: RR001A) (see FIG. 5 for the primer sequences and the PCR condition, S-OCp: sequence No. 15, AS-OCp: sequence No. 16), to give a 868-bp PCR product. It is subjected to electrophoresis and purification, and then ligated and inserted to PGEM-T Easy of T vector (Promega, catalogue No.: A1360) with the T4 DNA ligase as the OC promoter. The cloned OC promoter was confirmed to have a correct base sequence in a DNA sequencer, and then, cleaved from the vector by NotI digestion and blunted with T4 DNA polymerase. pΔPr.-E1A-CMV-19K and pΔPr.-E1AΔ24-CMV-19K were digested with SalI, blunted with T4 DNA polymerase, and additionally, treated with CIP while inserting the OC promoter in the ligation reaction with a T4 DNA ligase, to give pOC-E1A-CMV-19K and pOC-E1AΔ24-CMV-19K respectively. The pOC-E1A-CMV-19K and pOC-E1AΔ24-CMV-19K thus prepared were proliferation-regulated vector plasmids expressing E1A or E1AΔ24 by an OC promoter and E1B19K by a CMV promoter (see FIGS. 6 and 7).

Example 3

(Preparation of a Vector Plasmid Containing a Therapeutic Gene-expressing Unit)

A plasmid allowing insertion of a therapeutic gene freely into a proliferation-regulated vector plasmid previously or into a recombinant proliferation-regulated adenovirus vector plasmid afterward was prepared by using a Cre recombination reaction. A plasmid having an LoxP sequence that allows insertion of a therapeutic gene and the promoter thereof was prepared as follows: A Kn (kanamycin)-resistance gene of pUni/V5-HisC (Invitrogen, Carlsbad, Calif., Product Number: ET003-11) was cleaved with BglII (Toyobo, catalogue No.: BGL-211) and SmaI (Toyobo, catalogue No.: SMA-111), blunted with T4 DNA polymerase, and subjected to a CIP treatment for prevention of autoligation. The Tc (tetracycline) -resistance gene in pBR322 (Toyobo, catalogue No.: DNA-003) was digested with SspI (Toyobo, catalogue No.: SSP-101) and StyI (New England Biolabs, Beverly, Mass., catalogue No.: R0050S) and blunted with T4 DNA polymerase. The product was ligated and inserted to pUni/V5-HisC that had no Kn-resistant gene and was blunted similarly to above by using T4 DNA ligase, to give a vector plasmid containing a therapeutic gene-expressing unit pUni/V5-HisC-Tc in which the Kn-resistant gene was replaced with the Tc-resistance gene (see FIG. 8). In addition, the pUni/V5-HisC-Tc was digested with XhoI, blunted with T4 DNA polymerase, and subjected to a CIP treatment. Separately, as described above, DNA's obtained by cleaving the CMV promoter region prepared by amplifying a sense primer having a SalI site inserted by using a plasmid pRC/CMV as the template (S-CMVp, sequence No. 11) and an antisense primer having an MfeI site (AS-CMVp, sequence No. 12) by PCR with SalI and MfeI enzymes and blunting the products with T4 DNA polymerase, and the blunted pUni/V5-HisC-Tc were ligated with T4 DNA ligase, to give pUni/V5-HisC-Tc-CMV. Thus, the pUni/V5-HisC-Tc-CMV is a plasmid having a CMV promoter inserted in pUni/V5-HisC-Tc that allows insertion of a desirably expressed therapeutic gene to the region downstream of the CMV promoter by using any one of multicloning sites, AgeI, ApaI, and StuI. The CMV promoter and the gene inserted downstream thereof allows insertion of a therapeutic gene into the proliferation-regulated vector plasmid regulating the E1 region described in the former section by Cre expression or to the finally prepared proliferation-regulated adenoviral vector plasmid by Cre expression. The CMV promoter can be cleaved with restriction enzymes HincII and AgeI as needed, and a organ-specific promoter can be inserted thereto easily (see FIG. 8).

Example 4

(Preparation of a First Therapeutic Gene-expressing Vector Plasmid)

For example, a vector plasmid having an inserted marker gene EGFP (enhanced green-fluorescent protein) was prepared as follows: First, pEGFP-C1 (CLONETECH, catalogue No.: 6084-1) was digested with BclI and blunted with T4 DNA polymerase; and then, EGFP cDNA was cleaved by AgeI digestion. Separately, pUni/V5-HisC-Tc-CMV was digested with ApaI, blunted with T4 DNA polymerase, and digested with AgeI; and the cleaved EGFP cDNA fragment was ligated and inserted thereto with T4 DNA ligase, to give pUni/V5-HisC-Tc-CMV-EGFP. Thus, the first therapeutic gene-expressing vector plasmid pUni/V5-HisC-Tc-CMV-EGFP is an expression vector expressing EGFP from the CMV promoter and allowing insertion of the CMV-EGFP gene to the proliferation-regulated vector plasmid regulating the E1A region and the finally prepared proliferation-regulated adenoviral vector plasmid in the Cre recombination reaction (see FIG. 8). The EGFP is not a therapeutic gene but inserted as a substitute of therapeutic gene for convenience in experiment.

Example 5

(Recombination of a Proliferation-regulated Vector Plasmid and a First Therapeutic Gene-expressing Vector Plasmid, and Preparation of a Second Therapeutic Gene-expressing Vector Plasmid)

Figure 9:
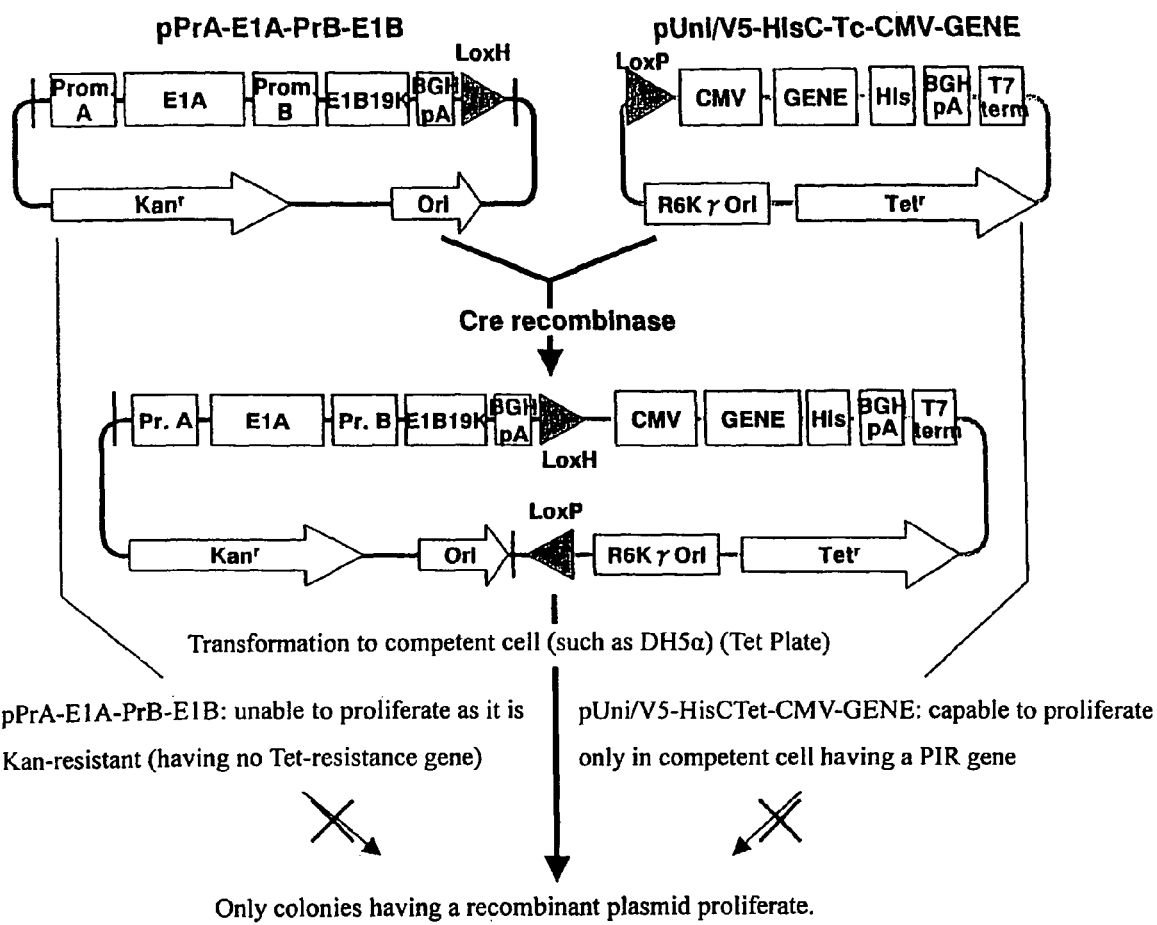
FIG. 9 is a figure showing the process of preparing the second therapeutic gene-expressing vector plasmid in Example 5 by recombination.

It is possible to recombine a proliferation-regulated vector plasmid (expressing E1A and E1B with various promoters) and a first therapeutic gene-expressing vector plasmid (expressing a therapeutic gene with various promoters) easily with a Cre recombinase (reaction of two plasmids binding to each other by recognizing the LoxP and LoxH sequences); and recombination experiments in the following eight combinations were performed as examples. Each of proliferation-regulated vector plasmids (pCEA-E1A-CMV-19K, pCEA-E1AΔ24-CMV-19K, pE2F-E1A-CMV-19K, pE2F-E1AΔ24-CMV-19K, pCEA-E1A-E2F-19K, pCEA-E1AΔ24-E2F-19K, pOC-E1A-CMV-19K, and pOC-E1AΔ24-CMV-19K) and a first therapeutic gene-expressing vector plasmid (pUni/V5-HisC-Tc-CMV-EGFP) in an amount of 100 ng was allowed to react with a Cre recombinase (Invitrogen, catalogue No.: R100-10) at 37° C. for 20 minutes. Then, the reaction was terminated by inactivating Cre by treatment at 65° C. for 5 minutes. The reaction solution was transformed into competent cells DH5α (Toyobo, catalogue No.: -DNA-903), and the resulting cell was incubated on an LB (Luria-Bertani, Nacalai Tesque, catalogue No.: 20066-95) agarose plate containing tetracycline (7.5 µg/ml, Wako Pure Chemical Industries, catalogue No.: 205-08591). The proliferation-regulated vector plasmid does not form colonies because it has a Kn-resistant gene, while the first therapeutic gene-expressing vector plasmid, which has a special Ori (*E. coli* replication origin) called R6Kγ, cannot form colonies of the DH5α cells. In contrast, the second therapeutic gene-expressing vector plasmid, which was prepared in recombination of a proliferation-regulated vector plasmid and the first therapeutic gene-expressing vector plasmid, forms colonies of DH5α cells, because it contains both UCOri and Tc$^r$, (see FIG. 9; in the Figure, the product in recombination of pPrA-E1A-PrB-E1B and pUni/V5-HisC-Tc-CMV-GENE is the second therapeutic gene-expressing vector plasmid). The reaction was performed by using a Cre recombinase purchased from Invitrogen (Invitrogen, catalogue No.: R100-10) at first, but there were no *E. coli* colonies formed on the LB plate. For confirmation of the correctness of the reaction system, a similar reaction was performed by using the plasmids pUni/V5-HisC and pcDNA4/HisMax-Ea attached to a cloning kit of Invitrogen (Echo cloning system, catalogue No.: ET401-30C), resulting in formation of five or less colonies. Thus, the activity of the Cre recombinase seemed to be low. Thus, the Cre recombinase was extracted by using an adenoviral vector AxCANCre expressing the Cre gene (provided from by the DNA bank of Riken Institute of Physical and Chemical Research). First, HepG2 cell, a human liver cancer cell higher in adenoviral gene-transferring efficiency (provided from by the Cell Research Center for Biomedical Research, Institute of Development, Aging and Cancer, Tohoku University), was infected onto a 10 cm-diameter culture dish at a concentration of 30 MOI (multiplicity of infection, 1 MOI: 1 plaque-forming unit/cell); the cells were removed after three days by trypsin (nacalai tesque, catalogue No.: 35555-54) treatment, washed with PBS, dissolved in 200 µl of a lysis buffer (containing 20 mM Tris at pH 7.5, 150 mM NaCl, 10 mM MgCl$_2$, 10% glycerol, and 1% protease inhibitor cocktail (SIGMA, catalogue No.: P2714)), and frozen and thawed repeatedly three times, to give a Cre recombinase for use. Reaction by using the Cre resulted in formation of colonies, and the colonies formed were all positive clones. The results showed that the Cre extracted with AxCANCre had a sufficient activity in the reaction system. The second therapeutic gene-expressing vector plasmids obtained in the reaction were named respectively pCEA-E1A-CMV-19K/CMV-EGFP, pCEA-E1AΔ24-CMV-19K/CMV-EGFP, pE2F-E1A-CMV-19K/CMV-EGFP, pE2F-E1AΔ24-CMV-19K/CMV-EGFP, pCEA-E1A-E2F-19K/CMV-EGFP, pCEA-E1AΔ24-E2F-19K/CMV-EGFP, pOC-E1A-CMV-19K/CMV-EGFP, and pOC-E1AΔ24-CMV-19K/CMV-EGFP.

Example 6

(Recombination to an Adenoviral Genome and Preparation of a Proliferation-regulated Adenoviral Vector Plasmid)

A proliferation-regulated adenoviral vector plasmid having no therapeutic gene was prepared, in addition to the second therapeutic gene-expressing vector plasmid (the Cre recombination described above), and the system and the function thereof were analyzed. A 30.3-kb plasmid pAdHM4 having an adenoviral genome (E1 region: 342 to 3523 bp, lacking part of E3 region 23133 to 30813 bp) (provided from by Dr. Mark A. Kay, Stanford University) has a sequence-recognizing restriction enzymes I-CeuI and PI-SceI in the deficient E1 region for insertion of foreign genes. pAdHM4 was first digested with a restriction enzyme I-CeuI (New England Biolabs, catalogue No.: R0699S) (0.2 U/μg DNA, 37° C., 1 hour), purified with phenol and chloroform, and then precipitated with ethanol. It was then digested with PI-SceI (New England Biolabs, catalogue No.: R0696S) and purified similarly. pCEA-E1A-CMV-19K, pCEA-E1AΔ24-CMV-19K, pE2F-E1A-CMV-19K, pE2F-E1AΔ24-CMV-19K, pCEA-E1A-E2F-19K, pCEA-E1AΔ24-E2F-19K, pOC-E1A-CMV-19K, and pOC-E1AΔ24-CMV-19K were digested with I-CeuI and PI-SceI and inserted to pAdHM4 respectively by using T4 DNA ligase. The plasmids obtained were always digested with I-CeuI and PI-SceI, and the inserted genes were confirmed. The proliferation-regulated adenoviral vector plasmids thus obtained were designated as pAd.HM4-CEA-E1A-CMV-19K, pAd.HM4-CEA-E1AΔ24-CMV-19K, pAd.HM4-E2F-E1A-CMV-19K, pAd.HM4F-E2F-E1AΔ24-CMV-19K, pAd.HM4-CEA-E1A-E2F-19K, pAd.HM4-CEA-E1AΔ24-E2F-19K, pAd.HM4-OC-E1A-CMV-19K, and pAd.HM4-OC-E1AΔ24-CMV-19K. These plasmids are plasmids having adenovirus genome regions other than E1 and E3 and an exogenous promoter having a region expressing the E1A and E1B19K regions.

Example 7

(Transfection to 293 Cells)

The proliferation-regulated adenoviral vector plasmid obtained in Example 6 was transfected to human fetal renal cell-derived 293 cells. The 293-cell culture solution used was DMEM (Dulbecco's Minimum Essential Medium, SIGMA, catalogue No.: D5796) containing inactivated 10% fetal bovine sera (MBL, catalogue No.: 268-1). Transfection was performed by a calcium phosphate method (Current Protocols in Molecular Biology, John Wiley & Sons, Inc., 9.1.4 to 9.1.9, 1999); a total of 40/μg of DNA's, 20 μg of linear chain DNA containing the adenoviral genome above and 20 μg of salmon testoid DNA (SIGMA, catalogue No.: D-7656), were added to 1.5 ml HEPES-buffered saline (pH7.1); 75 μl of 2.5 M $CaCl_2$ was added dropwise thereto while the solution was stirred, and the mixture was left at a room temperature for 30 minutes; and then, the culture solution was added dropwise to the 293 cells while the mixture was stirred. The mixture was incubated in a $CO_2$ incubator for 4 hours and 30 minutes; a solution containing a mixture of α-MEM (GIBCO BRL, catalogue No.: 12000-022) in 10% inactivated equine sera (GIBCO BRL, catalogue No.: 26050-088) and 1% agarose gel in the same amounts were piled up; and the 293 cells were incubated additionally on the solid culture medium. For evaluation of transfection efficiency, pEGFP-C1 was transfected in the same protocol and the positive cells were observed under a fluorescence microscope after 43 hours, showing that the gene was transfected to the cells at a rate of about 30% every time. When the adenovirus is produced, the 293 cells form plaques by the cytopathic effect (CPE). Traditional methods, in which adenoviruses are produced by homologous recombination, demanded transfection on a lot of culture dishes and a high gene-transferring efficiency, because of its low homologous recombination efficiency, but in the preparative method according to the present invention, which is based on an in-vitro ligation method (Mizuguchi H., et al., Hum. Gene Ther., 10, 2013-2017, 1993), 30 or more plaques appear on a 10-cm culture dish, and thus, a transfection efficiency of 30% is sufficient.

Example 8

(Two Modified Methods of Cloning a Proliferation-regulated Adenoviral Vector Plasmid Having a Therapeutic Gene Rapidly)

1. System of cloning a Therapeutic Gene Into a Proliferation-Regulated Adenoviral Vector Plasmid and a First Therapeutic Gene-expressing Vector Plasmid Directly by Cre Recombination.

It is possible to prepare ADV's in a greater number of combinations rapidly and easily by cloning, if it is possible to integrate only a therapeutic genetic freely after cloning a proliferation-regulated vector plasmid having no therapeutic gene (e.g., pCEA-E1A-CMV-19K) into an adenovirus vector plasmid (pAdHM4, etc.). To establish the system, a cloning experiment was done by using pAd.HM4-CEA-E1A-CMV-19K and pUni/V5-HisC-Tc-CMV-EGFP as an example. 100 ng respectively of the two plasmids were mixed and allowed to react with each other (37° C. for 20 minutes), by using the Cre recombinase purified as described above. Then, the reaction was terminated by inactivating Cre by treating the mixture at 65° C. for 5 minutes.

The reaction solution was transformed into competent cells DH5α (Toyobo, catalogue No.: DNA-903), and the cells were incubated on an LB (Luria-Bertani, Nacalai Tesque, catalogue No.:

20066-95) agarose plate containing tetracycline (7.5 μg/ml, Wako Pure Chemical Industries, catalogue No.: 205-08591). There were five colonies observed on the plate next day. Analysis of the plasmids obtained from the colony revealed that all plasmids were converted in recombination to proliferation-regulated adenoviral vector plasmids having a therapeutic gene pAd.HM4-CEA-E1A-CMV-19K/CMV-EGFP, to which the CMV-EGFP gene is to be inserted. A longer length of the adenoviral vector plasmid at 30 kb and an influence of the antibiotic tetracycline seem to be the reason for the smaller colony counts, but these results indicate that formation of at least one colony is sufficient because the probability of the insertion of the therapeutic gene is 100%. This modified method eliminates the need for inserting a therapeutic gene into a shuttle vector and then cloning it into an adenoviral vector, in comparing the effects of various therapeutic genes and their promoters while integrating the E1A and E1B promoters.

2. Cellular Cre Recombination by Cotransfection

The inventors have established a method of preparing an adenovirus having a therapeutic gene in recombination of two plasmids in the cell, by cotransfection the first therapeutic gene-expressing vector plasmid into a Cre-expressing cell without integrating the vector plasmid into the proliferation-regulated adenoviral vector plasmid pAd.HM4-CEA-E1A-CMV-19K or the like. pAd.HM4-CEA-E1A-CMV-19K and expressing EGFP gene as a marker pUni/V5-HisC-Tc-CMV-EGFP were cotransfected to 293 cells expressing constitutively Cre, respectively in amounts of 20 μg by the calcium phosphate method.

For evaluation of the gene-transferring efficiency, pEGFP-C1 expressing the EGFP gene plasmid was transfected by the same method; the culture medium was changed to a new one after 4 hours and a half; the cells were treated with trypsin and collected after 48 hours; the EGFP positive cells were counted under a fluorescence microscope, showing a positive rate (gene-transferring efficiency) of 21%. Plaques were formed after six days, and ten perfect plaques are formed after twelve days; and ten plaques were harvested after 14 days. Among these plaques, plaques of ADV having EGFP integrated in Cre recombination were EGFP-positive all over the plaques, when observed under a fluorescence microscope. In this experiment, one of the ten plaques was EGFP-positive, and thus, the probability of emergence of the EGFP-integrated ADV was 10%. A smaller number of plaques formed in the experimental system smaller than that by common ADV construction methods seems to a result of the decline in the efficiency of ADV production due to elimination of PacI digestion, because Cre recombination does not proceed when a plasmid containing an ADV genome DNA is converted to a straight chain DNA by digestion with a restriction enzyme PacI. A total of four plaque solutions, the EGFP(+) plaque solution and three EGFP(−) plaque solutions, were infected respectively to 293 cells in 24 wells and amplified therein. All cells in the wells became EGFP positive with the EGFP(+) clone, while only part of the cells became EGFP positive in other wells. CPE appeared in all clones after three days, and the cells were collected. The cells were infected to 293 cell in a 10-cm dish in the next step; approximately 50 to 60% of the EGFP(+) clones were EGFP positive one day after infection and all cells were CPE but only 80% of the cells were EGFP positive after two days. That is, the remaining 20% cells were converted to CPE by the ADV having no EGFP gene, suggesting that the plaques collected as monoclonal were actually contaminated with EGFP(−) ADV. For purification of the ADV, it would be effective to infect it into 293 cell once again and collect its EGFP-positive plaques.

In this manner, it was confirmed that it was possible to prepare an ADV having an inserted gene (EGFP gene) while the two plasmids were recombined in a Cre-expressing 293 cell by the cotransfection method. The method above is a method more convenient and rapid than a system consisting of in-vitro Cre reaction, transformation to *E. coli*, and transfection of the resulting plasmid.

Example 9

(Collection of a Proliferation-regulated Recombinant Adenoviral Vector from Plaques and Proliferation and Purification Thereof)

There were twelve plaques formed seven days after transfection of pAd.HM4-CEA-E1A-CMV-19K. A state when the cell disappeared completely in the center of a plaque and the bottom of the dish was observable was regarded as "complete plaque formation", and the plaques were collected together with the solid culture medium by using a 1,000-μl micropipetter chip which was previously broadened at the tip, resuspended in a 800-μl culture medium, and stored at −80° C. Ten plaques were collected for each virus.

Then, the suspension was thawed in a thermostat bath at 37° C. and frozen in liquid nitrogen repeatedly for three time, o give 600 μl of an adenoviral solution obtained by destructing the cell, which was then infected to the 293 cell that was grown previously in 24-well culture plate to a concentration of 1×10$^5$. After infection, 200 μl of the culture medium is added every three days, and CPE appears roughly in 5 to 7 days. After appearance of CPE, the culture medium and the cells were collected and stored at −80° C. Then, 800 μl of the solution (80% of total volume) was thawed and frozen similarly for three times, and infected to 70 to 80% confluent 293 cells on a 10-cm culture plate. In the stage, CPE appeared in 2 to 4 days, and the culture medium and the cell were collected and stored at −80° C. In the next stage, the solution was thawed and frozen similarly for three times, and 80% of the total volume (generally, 8 ml) was infected to 70 to 80% confluent 293 cells in 15-cm culture dishes (six dishes). After infection, CPE appeared in 2 to 3 days, and the culture medium and the cell were collected and stored at −80° C. Finally, the solution was thawed and frozen similarly for three times, and 80% of the total volume (generally, 100 ml) was infected to 70 to 80% confluent 293 cells on forty 15-cm culture dishes. CPE appeared generally in 2 days; the culture medium and the cell were collected and centrifuged at 1,000 rpm; after removal of the supernatant the cells were resuspended in PBS (phosphoric acid buffering saline) in an amount of 1.5 ml per 50 ml of the cell suspension; and cell suspension in an amount of 24 ml containing the cells on all 40 plates was stored at −80° C. (It is possible to amplify the cells once again by infecting the solution to forty 15-cm culture dishes, if a bottle containing 45 ml of the supernatant is preserved instead of discharged.) After repeated freezing and thawing of the cell suspension for three times, the mixture was centrifuged at 1,000 rpm; the supernatant was collected; and 6 ml of the viral solution was added to four cesium chloride (Wako Pure Chemical Industries, catalogue No.: 039-01955) density gradient solutions (1.5 g/ml CsCl: 0.5 ml, 1.35 g/ml CsCl: 3 ml, and 1.25 g/ml CsCl: 3 ml) placed in Hitachi ultracentrifuge tubes (Hitachi Koki, catalogue No.: S303276A) After balanced strictly with PBS, the tubes were centrifuged first at 10° C. and 35,000 rpm for 1 hour in a cooled high-speed centrifuge (Hitachi Koki, Himac CP65β) by using a swing rotor (Hitachi Koki, RPS40T). There were generally three bands observable and the lowest bluish white band contains the adenovirus, and thus, the layer was collected in an amount of 1 ml (up to 1.5 ml) after careful removal of the supernatant. Four tubes gave a viral solution in a total amount of approximately 4 ml (up to 6 ml). Then, the viral solution was placed in a centrifugal tube containing 6 ml of 1.35 g/ml CsCl, and ultracentrifuged at 10° C. and 35,000 rpm for 13 hours, while balanced strictly with a balance tube similarly containing 1.35 g/ml CsCl. The virus was detected as a single band, and all of the viral solution in an amount of 1 to 2 ml was collected, after removal of the supernatant.

The virus was then purified in a demineralization column as follows: the solution in the demineralization column (Bio-rad, Econopac 10DG, Product Number: 732-2011) was discharged and washed with 15 ml of PBS. X ml of the viral solution was added therein. The eluant from the column were collected in 1.5-ml microtubes numbered from 1 (Nos. 1 to 7)

in an amount of 1 ml. Then, (3-X) ml of PBS was added to the column, and the eluant was collected similarly in an amount of 1 ml. Further, 4 ml of PBS was added, and the eluant was collected similarly in an amount of 1 ml. In this manner, there were seven tubes obtained, and most of the concentrated virus was contained in the fourth tube. For confirmation, the ADV concentration in all tubes was determined by the following method. 94 µl of PBS, 5 µl of 10% SDS, and 1 µl of the viral solution were mixed and agitated well with Voltex (SCIENTIFIC INDUSTRIES, Inc., BOHEMIA, MY), to destroy its viral envelope. The resulting solution was centrifuge at 15,000 rpm for 3 minutes; the supernatant was removed; and the $OD_{260\ nm}$ of the solution is determined. The concentration of the viral solution was calculated according to the following equation: 1 $OD_{260\ nm}$=1×10$^{12}$ particle/ml (1 $OD_{260\ nm}$=2× 10$^{13}$ particle/ml when diluted 20 times). Generally, when the viral solution was amplified on forty 15-cm culture dishes, 1.5 to 2 ml of viral solution at a concentration of 1 to 5×10$^{12}$ particle/ml was obtained.

The ADV solution after purification was divided into smaller aliquots together with 10% glycerol (Wako Pure Chemical Industries, catalogue No.: 075-00616), and the glycerol solutions were stored at −30° C. In this manner, eight kinds of adenoviruses, Ad.CEA-E1A-CMV-19K, Ad. E2F-E1A-CMV-19K, Ad. E2F-E1AAd.CEA-E1AΔ24-CMV-19K, Ad.E2F-E1A-CMV-19K, Ad.E2F-E1AΔ24-CMV-19K, Ad.CEA-E1A-E2F-19K, Ad.CEA-E1AΔ24-E2F-19K, Ad.OC-E1A-CMV-19K, and Ad.OC-E1AΔ24-CMV-19K were obtained.

Example 10

(Confirmation of Proliferation of the Proliferation-regulated Recombinant Adenoviral Vector Prepared)

CEA promoter-dependent proliferation of Ad.CEA-E1A-CMV-19K was studied as an example. Ad.CEA-E1A-CMV-19K was infected to a CEA-expressing colon-cancer cell line colo-205, Lovo, HCT-15 cells (provided from by the Cell Research Center for Biomedical Research, Institute of Development, Aging and Cancer, Tohoku University), non-CEA-expressing Hela cells, and a positive control 293 cells in which all adenoviruses proliferate, respectively at MOI's of 100, 10, 1, 0.1, 0.01, and 0, and appearance of CPE was observed. All cells in the wells infected at an MOI of 100 showed strong cytotoxicity 2 days after infection. In contrast, the wells infected with an nonproliferating (E1-deficient) ADV, Ad.CMV-LacZ, showed only slight cytotoxicity at an MOI of 100, indicating that viral proliferation was already initiated in the CEA-expressing colon-cancer cell line. Seven days after infection, Lovo and 293 cells showed CPE down to MOI 1, HCT-15 cells showed CPE down to MOI 10, colo-205 cells showed a slight cytotoxicity at MOI 100, Hela cells showed CPE only at MOI 100, Lovo and 293 cells allowed proliferation of ADV in the same degree, HCT-15 cells also allowed proliferation in a degree slightly lower than those above, and thus, colo-205 and Hela cells seemed to have no significant difference in allowing proliferation of ADV. Finally 2 weeks after infection, Lovo cells showed cell injury down to MOI 0.1; HCT-15 cells, down to MOI 1; and 293 cells, down to MOI 0.01; which reflects the degree of ADV proliferation. In contrast, the fact that colo-205 cells did not show cell injury even at an MOI of 100 and Hela cells did not show cell injury down to MOI 10 seemed to be because proliferation of ADV was regulated by the CEA promoter. However, it is necessary to evaluate the proliferation of ADV continuously over time, to judge whether the some cell injury observed of non-CEA-producing cancerous Hela cells is due to proliferation of ADV or sensitivity of the Hela cells. Thus, an EGFP gene was introduced into the vector to which a therapeutic gene is integrated as a marker, to give Ad.CEA-E1A-CMV-19K/CMV-EGFP. It is possible to study proliferation of this ADV, by monitoring the positive rate of EGFP after infection to cell. In the following Table 1, shown are the data concerning the proliferation potential of the proliferation-regulated recombinant adenoviral vectors 12 days after infection as expressed by cell death (CPE). Both in Tables 2 and 3, the term "intact" means unchanged (without injury).

TABLE 1

| | MOI | | | | | |
|---|---|---|---|---|---|---|
| | 100 | 10 | 1 | 0.1 | 0.01 | 0 |
| Lovo | CPE | CPE | CPE | Cell injury | intact | intact |
| HCT-15 | CPE | CPE | Cell injury | intact | intact | intact |
| Colo-205 | intact | Intact | intact | intact | intact | intact |
| 293 | CPE | CPE | CPE | CPE | Cell injury | intact |
| Hela | CPE | Cell injury | intact | intact | intact | intact |

Example 11

(Proliferation-regulated Recombinant Adenoviral Vector Expressing EGFP)

Ad.CEA-E1A-CMV-19K/CMV-EGFP was prepared according to a method similar to above and purified by ultracentrifugation, to give 2 ml of a viral solution at a concentration of 2.0×10$^{12}$ particle/ml. The viral solution was infected to CEA-expressing cancer cells MKN-1, MKN-28, MKN-45, HCT-15, Lovo, and colo-205 respectively at MOI's of 100, 10, 1, 0.1, 0.01, and 0, and proliferation of ADV's was evaluated with occurrence of cell injury (CPE) while observing the EGFP positive rate under a fluorescence microscope. Two days after infection all cells except colo-205 were almost 100% EGFP-positive at MOI 100, and only colo-205 cells were EGFP-positive at about 50%, indicating that the gene-transferring efficiency by ADV is lower to colo-205. Both the EGFP-positive rate and CPE increases in all cells over time, and the tendency was greatest when the cells were MKN-28, Lovo, and HCT-15. For example, in the results with MKN-28, about 20% cells were EGFP-positive and there was no cell injury at all in the well at MOI 1 one day after infection; the EGFP positive rate increased to about 50% after six days; there was cell injury (part of the cells became CPE) observed after eight days; and 80% or more of the cells turned to be positive and in the state almost close to CPE after twelve days. That is, a significant correlation observed between proliferation of ADV observable with marker gene EGFP and CPE corresponding to cell injury demonstrated that Ad.CEA-E1A-CMV-19K/CMV-EGFP proliferated in CEA-producing cancer cells and lead to death of the cells. The following Tables 2 and 3 are respectively those showing the proliferation potential of proliferation-regulated recombinant adenoviral vectors 12 days after infection as a function of EGFP-positive rate, and the proliferation potential 12 days after infection as a function of cell death (CPE).

TABLE 2

| | MOI | | | | | |
|---|---|---|---|---|---|---|
| | 100 | 10 | 1 | 0.1 | 0.01 | 0 |
| MKN-1 | 100% | 100% | 30% | 5% or less | 1% or less | 0 |
| MKN-28 | 100% | 100% | 80% | 20% | 1% or less | 0 |
| MKN-45 | 100% | 100% | 100% | 30% | 5% or less | 0 |
| HCT-15 | 100% | 100% | 100% | 80% | 20% | 0 |
| LOVO | 100% | 100% | 100% | 100% | 10% | 0 |
| Colo-25 | 50% | 30% | 10% or less | 1% or less | 1% or less | 0 |
| 293 | 100% | 100% | 100% | 100% | 100% | 0 |

TABLE 3

| | MOI | | | | | |
|---|---|---|---|---|---|---|
| | 100 | 10 | 1 | 0.1 | 0.01 | 0 |
| MKN-1 | CPE | Cell injury | intact | intact | intact | intact |
| MKN-28 | CPE | CPE | CPE | Cell injury | intact | intact |
| MKN-45 | CPE | CPE | intact | intact | intact | intact |
| HCT-15 | CPE | CPE | CPE | Cell injury | intact | intact |
| LOVO | CPE | CPE | CPE | CPE | intact | intact |
| Colo-25 | Cell injury | Intact | intact | intact | intact | intact |
| 293 | CPE | CPE | CPE | CPE | CPE | intact |

INDUSTRIAL APPLICABILITY

The method of preparing a proliferation-regulated recombinant adenoviral vector efficiently according to the present invention, which permits insertion of a promoter expressing only in a target organ in adenovirus easily, allows efficient and rapid preparation of an adenoviral vector target organ that does not proliferate in organs other than those targeted but proliferates specifically only in the target organ guided by multiple tissue-specific factors, and suppresses proliferation of cancer cell or the like. In addition, the method of preparing a proliferation-regulated recombinant adenoviral vector having an integrated therapeutic gene efficiently according to the present invention, which allows easy insertion of a promoter expressing only in a targeted organ and a therapeutic gene in adenovirus, allows efficient and rapid preparation of an adenoviral vector target organ that does not proliferate in organs other than those targeted but proliferates specifically only in the target organ guided by multiple tissue-specific factors, suppresses proliferation of cancer cell or the like, and introduces a selectively therapeutic gene into the target organ.

Thus, the present invention allows easy preparation and analysis of an multifactorial adenoviral vector completely specific to cancer by introducing various proliferation-regulated recombinant adenoviral vectors freely and efficiently, and rapidly, and is also applicable widely to the biological study on the fundamental problem on what is the difference between normal and cancer cells and other basic studies on cancer.

In addition, the preparative kit according to the present invention allows preparation of a proliferation-regulated recombinant adenoviral vector having an arbitrary promoter expressing only in target cells or a proliferation-regulated recombinant adenoviral vector having an arbitrary therapeutic gene.

The present invention is not limited to the Examples above, and any modifications of the present invention are also included in the present invention, if they are essentially within the scope of the invention.

The invention claimed is:

1. A method of preparing a proliferation-regulated recombinant adenoviral vector, comprising the steps of: preparing a proliferation-regulated plasmid by (a) preparing an expression cassette in a plasmid that includes, in order from upstream to downstream, an E1A region, at least one protein-coding region in a E1B region or the entire E1B region, a poly(A) signal sequence, and a recombinase-recognizing sequence, by replacing an endogenous promoter in the E1A region and an endogenous promoter regulating expression of a protein-coding gene in the at least one protein-coding region in the E1B region with a first and a second multiple cloning site, respectively, and (b) introducing a first and a second promoter, each of which expresses specifically in a target organ, into the first and second multiple cloning sites, respectively; and integrating the proliferation-regulated plasmid into a plasmid containing an E1 region-deleted adenoviral genome.

2. The method of claim 1, wherein the E1A region lacks a Rb protein-binding sequence.

3. The method of claim 2, wherein the protein-coding region in the E1B region includes a 19KDa protein-coding region.

4. The method of claim 1, wherein the first or the second multiple cloning site includes a blunt-end restriction enzyme site.

5. The method of claim 1, wherein the recombinase-recognizing sequence is LoxP, LoxH, or a mutant sequence thereof.

6. A method of preparing a proliferation-regulated recombinant adenoviral vector having an integrated therapeutic gene, comprising the steps of: (a) preparing a proliferation-regulated plasmid by (i) preparing an expression cassette in a plasmid that includes, in order from upstream to downstream, an E1A region, at least one protein-coding region in a E1B region or the entire E1B region, a poly(A) signal sequence, and a recombinase-recognizing sequence, by replacing an endogenous promoter in the E1A region and an endogenous promoter regulating expression of a protein-coding gene in the at least one protein-coding region in the E1B region with a first and a second multiple cloning site, respectively, and (ii) introducing a first and a second promoter, each of which expresses specifically in a target organ, into the first and second multiple cloning sites, respectively; (b) preparing a first therapeutic gene-expressing plasmid by (i) preparing a therapeutic gene expression cassette by inserting into a plasmid in order from upstream to downstream a recombinase-recognizing sequence and a third multiple cloning site, (ii) inserting, in order from upstream to downstream, a constitutive strong promoter or a therapeutic gene-expressing promoter and a therapeutic gene into the third multiple cloning site; (c) preparing a second therapeutic gene-expressing plasmid by allowing a recombinase to react with the proliferation-regulated plasmid and the first therapeutic gene-expressing plasmid; and (d) integrating the second therapeutic gene-expressing plasmid into a plasmid containing an E1 region-deleted adenoviral genome.

7. The method of claim 6, wherein the E1A region lacks a Rb protein-binding sequence.

8. The method of claim 7, wherein the protein-coding region in the E1B region includes a 19KDa protein-coding region.

9. A method of preparing a proliferation-regulated recombinant adenoviral vector having an integrated therapeutic gene, comprising the steps of: (a) preparing a proliferation-regulated adenoviral vector by (i) obtaining a proliferation-regulated plasmid by preparing an expression cassette in a plasmid that includes, in order from upstream to downstream, an E1A region, at least one protein-coding region in a E1B region or the entire E1B region, a poly(A) signal sequence, and a recombinase-recognizing sequence, by replacing an endogenous promoter in the E1A region and an endogenous promoter regulating expression of a protein-coding gene in the at least one protein-coding region in the E1B region with a first and a second multiple cloning site, respectively, and introducing a first and a second promoter, each of which expresses specifically in a target organ, into the first and second multiple cloning sites, respectively, and (ii) integrating the proliferation-regulated plasmid into a plasmid containing an E1 region-deleted adenoviral genome; (b) preparing a therapeutic gene-expressing plasmid by (i) preparing a therapeutic gene expression cassette by inserting into a plasmid in order from upstream to downstream a recombinase-recognizing sequence and a third multiple cloning site, (ii) inserting, in order from upstream to downstream, a constitutive strong promoter or a therapeutic gene-expressing promoter and a therapeutic gene into the third multiple cloning site; and (c) allowing a recombinase to react with the proliferation-regulated adenoviral vector and the therapeutic gene-expressing plasmid.

10. The method of claim 9, wherein the E1A region lacks a Rb protein-binding sequence.

11. The method of claim 10, wherein the protein-coding region in the E1B region includes a 19KDa protein-coding region.

12. The method of claim 9, wherein step (c) is accomplished by mixing the proliferation-regulated adenoviral vector of step (a) and the therapeutic gene-expressing plasmid of step (b), allowing a recombinase to react with the mixture, and then transforming the mixture into a cell.

13. The method of claim 9, wherein step (c) is accomplished by cotransfecting the proliferation-regulated adenoviral vector of step (a) and the therapeutic gene-expressing plasmid of step (b) into a recombinase-expressing cell.

14. The method of claim 13, wherein the recombinase-expressing cell is prepared by making an adenoviral E1-region protein-expressing cell additionally express a recombinase.

15. The method of claim 6, wherein the recombinase-recognizing sequence in the first therapeutic gene-expressing plasmid is different from the recombinase-recognizing sequence in the proliferation-regulated plasmid.

16. The method of claim 15, wherein the E1A region lacks a Rb protein-binding sequence.

17. The method of claim 16, wherein the protein-coding region in the E1B region includes a 19KDa protein-coding region.

18. The method of claim 6, wherein a drug tolerance gene in the proliferation-regulated plasmid and a drug tolerance gene in the first therapeutic gene-expressing plasmid are different from each other, and Ori in the first therapeutic gene-expressing plasmid can duplicate pir genes such as $R6K_{65}$ only in competent cell.

19. The method of claim 18, wherein the E1A region lacks a Rb protein-binding sequence.

20. The method of claim 19, wherein the protein-coding region in the E1B region includes a 19KDa protein-coding region.

* * * * *